(12) United States Patent
Shin et al.

(10) Patent No.: US 10,596,376 B2
(45) Date of Patent: Mar. 24, 2020

(54) STIMULATION OF THE VENTRAL PALLIDUM FOR THE TREATMENT OF EPILEPSY

(71) Applicant: ALBANY MEDICAL COLLEGE, Albany, NY (US)

(72) Inventors: Damian Seung-Ho Shin, Slingerlands, NY (US); Wilson Jonathan Yu, Eden Prairie, MN (US)

(73) Assignee: ALBANY MEDICAL COLLEGE, Albany, NY (US)

(*) Notice: Subject to any disclaimer, the term of this patent is extended or adjusted under 35 U.S.C. 154(b) by 158 days.

(21) Appl. No.: 15/760,736

(22) PCT Filed: Sep. 15, 2016

(86) PCT No.: PCT/US2016/051862
§ 371 (c)(1),
(2) Date: Mar. 16, 2018

(87) PCT Pub. No.: WO2017/048908
PCT Pub. Date: Mar. 23, 2017

(65) Prior Publication Data
US 2018/0250512 A1    Sep. 6, 2018

Related U.S. Application Data

(60) Provisional application No. 62/219,847, filed on Sep. 17, 2015.

(51) Int. Cl.
*A61N 1/36* (2006.01)
*A61N 1/05* (2006.01)

(52) U.S. Cl.
CPC ....... *A61N 1/36064* (2013.01); *A61N 1/0534* (2013.01); *A61N 1/36146* (2013.01);
(Continued)

(58) Field of Classification Search
CPC .......... A61N 1/05; A61N 1/0534; A61N 1/36; A61N 1/36146; A61N 1/36153;
(Continued)

(56) References Cited

U.S. PATENT DOCUMENTS

6,227,203 B1 * 5/2001 Rise ................. A61M 5/14276
128/898
6,819,956 B2   11/2004 DiLorenzo
(Continued)

OTHER PUBLICATIONS

International Search Report and Written Opinion Form PCT/ISA/220, International Application No. PCT/US 16/51862 pp. 1-7, dated Oct. 26, 2016, dated Dec. 1, 2016.

*Primary Examiner* — Christopher A Flory
(74) *Attorney, Agent, or Firm* — Bond Schoeneck and King PLLC; David Nocilly

(57) ABSTRACT

Deep brain stimulation of the ventral pallidum (VP-DBS) prevents or potently attenuates epileptiform activity and behavioral seizures. VP-DBS prior to pilocarpine prevented behavioral partial and generalized forebrain seizures and generalized brainstem seizures in most animals. VP-DBS after brainstem seizures emerged prevented or reduced the appearance of subsequent behavioral and electrographic brainstem seizures. Even if VP-DBS was turned on after partial forebrain seizures started, this timed approach could still reduce partial forebrain seizures but also prevented secondarily generalized forebrain seizures. Epileptiform activity in brainstem areas, especially in the nucleus of the solitary tract (NTS) which controls cardiovascular function, was prevented by VP-DBS. Altogether, VP-DBS is a therapeutic approach for individuals with intractable epilepsy with partial and/or generalized seizures and may potentially prevent or diminish sudden unexpected death in epilepsy (SUDEP) by preserving activity of brain stem neurons involved in cardio-respiratory function.

2 Claims, 18 Drawing Sheets

Figures 1A, 1B:
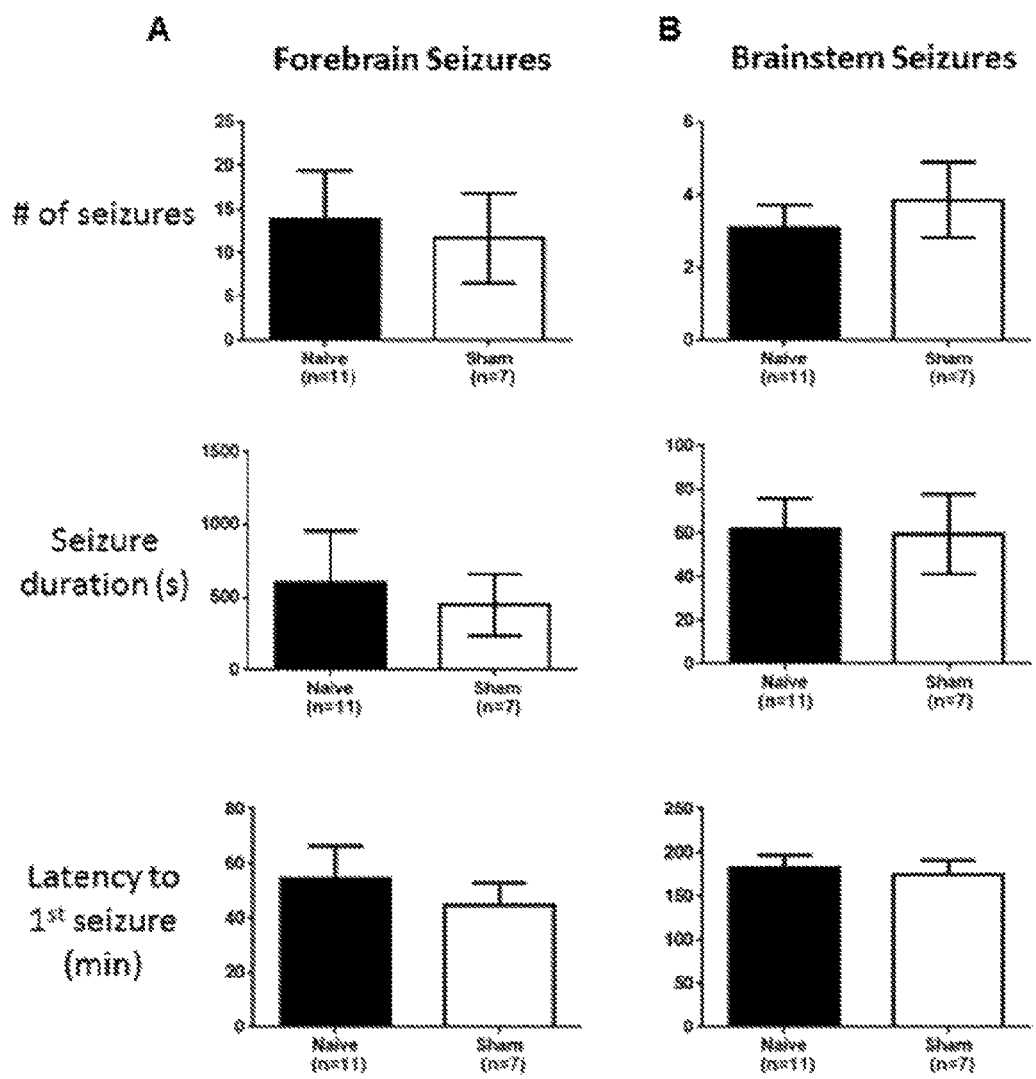

(52) U.S. Cl.
CPC ..... *A61N 1/36171* (2013.01); *A61N 1/36175* (2013.01); *A61N 1/36153* (2013.01); *A61N 1/36157* (2013.01); *A61N 1/36167* (2013.01); *A61N 1/36178* (2013.01)

(58) Field of Classification Search
CPC ............ A61N 1/36157; A61N 1/36167; A61N 1/36171; A61N 1/36175; A61N 1/36178
See application file for complete search history.

(56) References Cited

U.S. PATENT DOCUMENTS

| | | | |
|---|---|---|---|
| 7,499,752 B2 | 3/2009 | Maschino et al. | |
| 7,555,344 B2 | 6/2009 | Maschino et al. | |
| 2002/0177882 A1* | 11/2002 | DiLorenzo | A61B 5/048 607/45 |
| 2002/0183817 A1* | 12/2002 | Van Venrooij | A61N 1/0534 607/116 |
| 2004/0172091 A1 | 9/2004 | Rezai | |
| 2005/0055064 A1* | 3/2005 | Meadows | A61N 1/36082 607/45 |
| 2005/0240242 A1* | 10/2005 | DiLorenzo | A61N 1/3605 607/45 |
| 2006/0217781 A1* | 9/2006 | John | G16H 50/50 607/45 |
| 2007/0043401 A1* | 2/2007 | John | G16H 50/50 607/45 |
| 2007/0073355 A1* | 3/2007 | Dilorenzo | A61N 1/3605 607/45 |
| 2007/0100392 A1* | 5/2007 | Maschino | A61M 5/14276 607/45 |
| 2008/0275526 A1* | 11/2008 | Lozano | A61N 1/36082 607/45 |
| 2009/0234419 A1* | 9/2009 | Maschino | A61M 5/14276 607/45 |
| 2010/0114272 A1* | 5/2010 | Haidarliu | A61B 5/04001 607/115 |
| 2010/0204748 A1* | 8/2010 | Lozano | A61B 5/04001 607/45 |
| 2010/0280572 A1* | 11/2010 | Meadows | A61N 1/36082 607/45 |
| 2010/0312303 A1* | 12/2010 | York | A61N 1/3605 607/45 |
| 2011/0184487 A1* | 7/2011 | Alberts | A61N 1/0534 607/45 |
| 2011/0184489 A1* | 7/2011 | Nicolelis | A61N 1/36025 607/48 |
| 2011/0307030 A1* | 12/2011 | John | A61N 1/36017 607/45 |
| 2012/0116211 A1* | 5/2012 | McIntyre | A61N 1/36082 600/416 |
| 2012/0116244 A1* | 5/2012 | McIntyre | A61N 1/36067 600/554 |
| 2012/0310298 A1 | 12/2012 | Besio et al. | |
| 2013/0172716 A1* | 7/2013 | Lozano | A61B 5/04001 600/378 |
| 2013/0238059 A1* | 9/2013 | York | A61N 1/3605 607/74 |
| 2013/0289683 A1* | 10/2013 | Parker | A61N 1/025 607/116 |
| 2014/0288620 A1* | 9/2014 | DiLorenzo | A61N 1/36053 607/62 |
| 2015/0148878 A1 | 5/2015 | Yoo et al. | |
| 2015/0343215 A1 | 12/2015 | De Ridder | |
| 2016/0250473 A1* | 9/2016 | Alberts | A61N 1/0534 607/45 |
| 2016/0367809 A1* | 12/2016 | Patel | A61N 1/36064 |
| 2016/0367812 A1* | 12/2016 | De Ridder | A61N 1/36139 |

* cited by examiner

STIMULATION OF THE VENTRAL PALLIDUM FOR THE TREATMENT OF EPILEPSY

CROSS-REFERENCE TO RELATED APPLICATIONS

The present application claims priority to U.S. Provisional Application No. 62/219,847, filed on Sep. 17, 2015.

BACKGROUND OF THE INVENTION

1. Field of the Invention

The present invention relates to the treatment of patients with refractory epilepsy with or without risk for sudden unexpected death in epilepsy and, more particularly, to stimulation of the ventral pallidum.

2. Description of the Related Art

Antiepileptic drugs (AEDs) are the first line of treatment for individuals with epilepsies, but 30% are considered intractable. The most common intractable form of epilepsy is temporal lobe epilepsy (TLE), which can secondarily generalize to other brain areas to manifest generalized tonic-clonic seizures (GTCSs). Notably, GTCSs poses the greatest risk for seizure-related injuries and is accompanied by pronounced cardio-respiratory dysfunction, which are contributors for sudden unexpected death in epilepsy (SUDEP). The incidence of SUDEP is about 1 case for every 1,000 people with epilepsy. Epileptics with uncontrolled or frequent seizures and/or generalized convulsive (tonic-clonic or grand mal) seizures are generally at greater risk for SUDEP.

One conventional option for patients is pharmacological treatment; however 25-35% of patients are not adequately treated with AEDs. For intractable patients, an alternative option is resective surgery, which can reduce seizures with low morbidity in adults with TLE. However, some still have seizures despite this approach, while others are not candidates for surgery. Alternatively, deep brain stimulation (DBS) is a promising therapeutic for seizure control. At present, only vagus nerve stimulation (VNS) and Neuropace responsive Neurostimulation® (RNS) are FDA-approved for epilepsy. Both can reduce seizure frequencies; particularly partial seizures. Yet, both approaches offer little efficacy in seizure-freedom. Accordingly, there is a need in the art for a treatment for epilepsy that can reduce the incidence of SUDEP and provide freedom from partial and/or generalized seizures.

BRIEF SUMMARY OF THE INVENTION

The present invention comprises the use of deep brain stimulation of the ventral pallidum (VP-DBS) to attenuate or prevent epileptiform activity and behavioral seizures. VP-DBS (50 Hz) was applied to pilocarpine-treated rats prior to the appearance of generalized forebrain seizures or after generalized brainstem seizures manifested. VP-DBS prior to pilocarpine prevented behavioral partial and generalized forebrain seizures and generalized brainstem seizures in most animals, and VP-DBS after brainstem seizures emerged prevented or reduced the appearance of subsequent behavioral brainstem seizures. Furthermore, VP-DBS was still able to reduce subsequent partial seizure severity and prevented the transition to generalized forebrain seizures even after it was turned on after partial forebrain seizures started. Even after VP-DBS was applied when generalized forebrain seizures started, this approach was still able to reduce subsequent generalized forebrain seizures and prevented the transition to generalized brainstem seizures. We also applied VP-DBS prior to administration of pentylenetetrazol (PTZ) and throughout the monitored period. PTZ at the dosage we used induces GTCSs. Notably, VP-DBS markedly increased the latency for GTCSs to appear at unprecedented best-in-class values. Altogether, VP-DBS can be a novel therapeutic approach for individuals with intractable partial and generalized epilepsies and potentially prevent or diminish SUDEP by preserving activity of brainstem neurons involved in cardio-respiratory function. For example, a stimulator for performing VP-DBS may be implanted in people diagnosed with uncontrolled grand mal (more recently coined as "GTCSs") or temporal lobe epilepsy with or without secondarily generalized tonic-clonic seizures and the stimulator would be turned on and left on constantly or intermittently in a closed-loop system to provide best-in-class efficacy to provide seizure-freedom for individuals with intractable partial and generalized seizure with adjunctive efficacy to prevent SUDEP.

The present invention was confirmed by recording GABAergic VP neurons in brain slices and found that 50 Hz stimulation increased firing activity from 3.1±1.4 Hz to 7.6±1.7 Hz (n=8, p=0.008). The pilocarpine rat model of temporal lobe epilepsy (TLE) was used to determine whether VP stimulation could be antiepileptic. After pilocarpine injection, animals exhibited forebrain seizures, which generalized to the brainstem (n=9). 50 Hz VP-DBS prior to pilocarpine injection prevented epileptiform activity in the somatosensory cortex (S1) and attenuated forebrain seizures; in addition, no brainstem seizures occurred (n=9). In another set of experiments, VP-DBS was turned on after forebrain seizures generalized to the brainstem. Forebrain seizures and epileptiform activity in the primary sensory cortex (S1 region) still persisted, but brainstem seizures were completed abolished (n=9). Other experiments involved applying VP-DBS prior to pilocarpine and throughout the monitored period which prevent forebrain partial seizures. Moreover, VP-DBS immediately after the first generalized forebrain seizure appeared was still able to attenuate subsequent generalized forebrain seizures (n=12) and prevent the transition and appearance of generalized brainstem seizures (n=12). Notably, VP-DBS applied immediately after rats exhibited their first partial forebrain seizure was able to prevent the transition and emergence of seizures into generalized forebrain seizures (n=12) and was still able to reduce the duration of partial forebrain seizure (n=12). We also applied VP-DBS prior to administration of PTZ which induces GTCSs in rats at 90 mg/kg. VP-DBS markedly increased the latency for GTCSs to appear at unprecedented best-in-class values (n=12). To examine how VP-DBS could prevent seizure generalization to the brainstem, single-unit recordings were performed in the substantia nigra pars reticulata (SNR) and superior colliculus (SC) in anesthetized animals; these two structures are connected areas to the VP and involved in brainstem seizure symptomology. VP-DBS at 50 Hz decreased SNR and SC spiking activity from 25.4 Hz to 18.2 Hz (n=6) and 18.2 Hz to 11.0 Hz (n=18), respectively, in vivo. Whether VP-DBS could mitigate dysfunction in cardiovascular activity was also investigated, which would lend strong credence that this neuromodulatory approach could protect against SUDEP. Here, we monitored epileptiform activity in the nucleus of the solitary tract (NTS) which is a brainstem area that controls cardiac function. Prior to pilocarpine, heart rate waveforms (HRWs) were normal. After pilocarpine injection, we noted epileptiform activity in the S1 cortex and the appearance of sparse abnormal HRWs with 0.5±0.5 (n=4) of these per minute. Later, epileptiform activity also manifested in the NTS and these became synchronized with cortical seizures. During this time, the occurrence of abnormal HRWs increased markedly to 117.4±68.7 per min (n=4). However, when VP-DBS was turned on, epileptiform activity was prevented in the NTS, which coincided with only 44 abnormal HRWs per minute (n=1). Altogether, VP-DBS may prevent seizure generalization to the brainstem and in areas such as the NTS. This is notable given the NTS's importance in controlling cardiovascular function. Preliminary but provocative and cogent findings strongly posit that VP-DBS is a novel and promising stimulation target for the treatment of epilepsy and innovative neuromodulatory approach for mitigating or reducing SUDEP occurrences.

BRIEF DESCRIPTION OF THE SEVERAL VIEWS OF THE DRAWING(S)

Figure 1C:
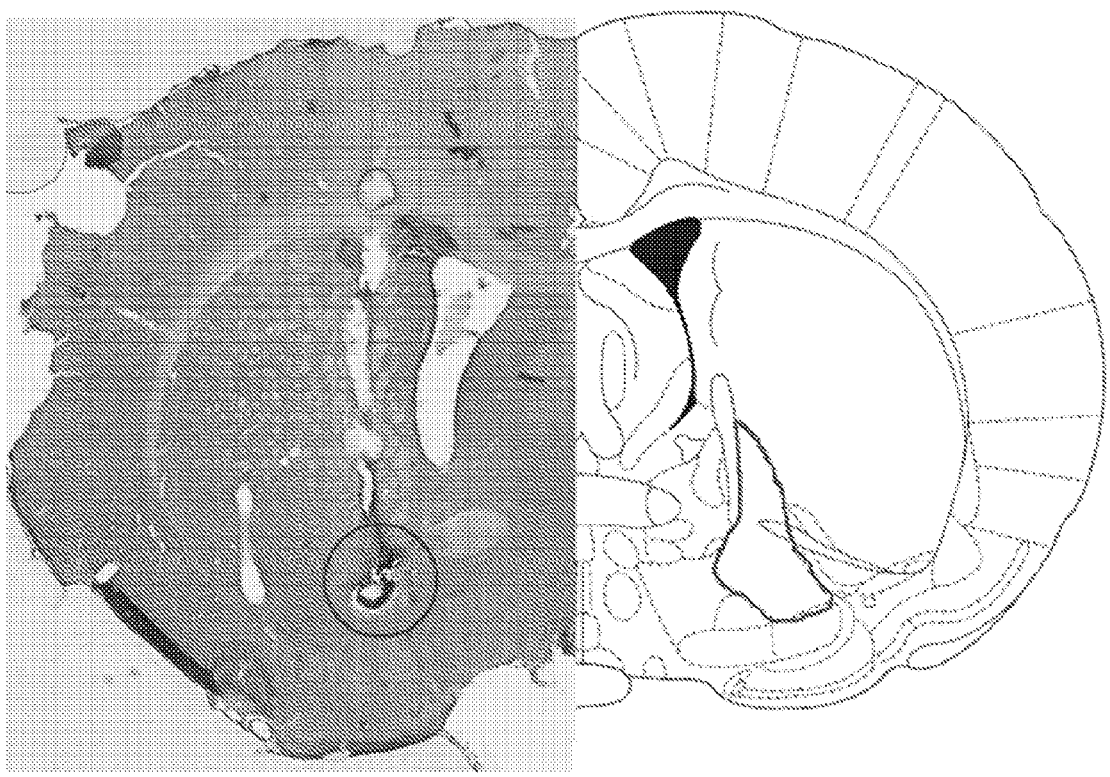

The present invention will be more fully understood and appreciated by reading the following Detailed Description in conjunction with the accompanying drawings, in which:

FIGS. 1A and 1B are a series of graphs showing that electrode implantation alone does not affect seizures. Naïve (n=11) and sham (n=7) rats were IP-injected with 40 mg/kg pilocarpine and behavioral seizures were recorded for 4 hours. Only sham rats had bilateral stimulating electrodes implanted in the VP, but these were not turned on during the entire monitoring period. Generalized forebrain seizure data are represented in FIG. 1A and generalized brainstem seizure in FIG. 1B. Number of seizures (top row), total seizure duration (middle row) and latency to $1^{st}$ seizure (bottom row) are shown. FIG. 1C shows a unilateral brain slice with the electrode placement in the VP is shown in red, opposite the corresponding section from a rat atlas (Paxinos, 1998) with the target brain area outlined in red.

Figures 2A, 2B:
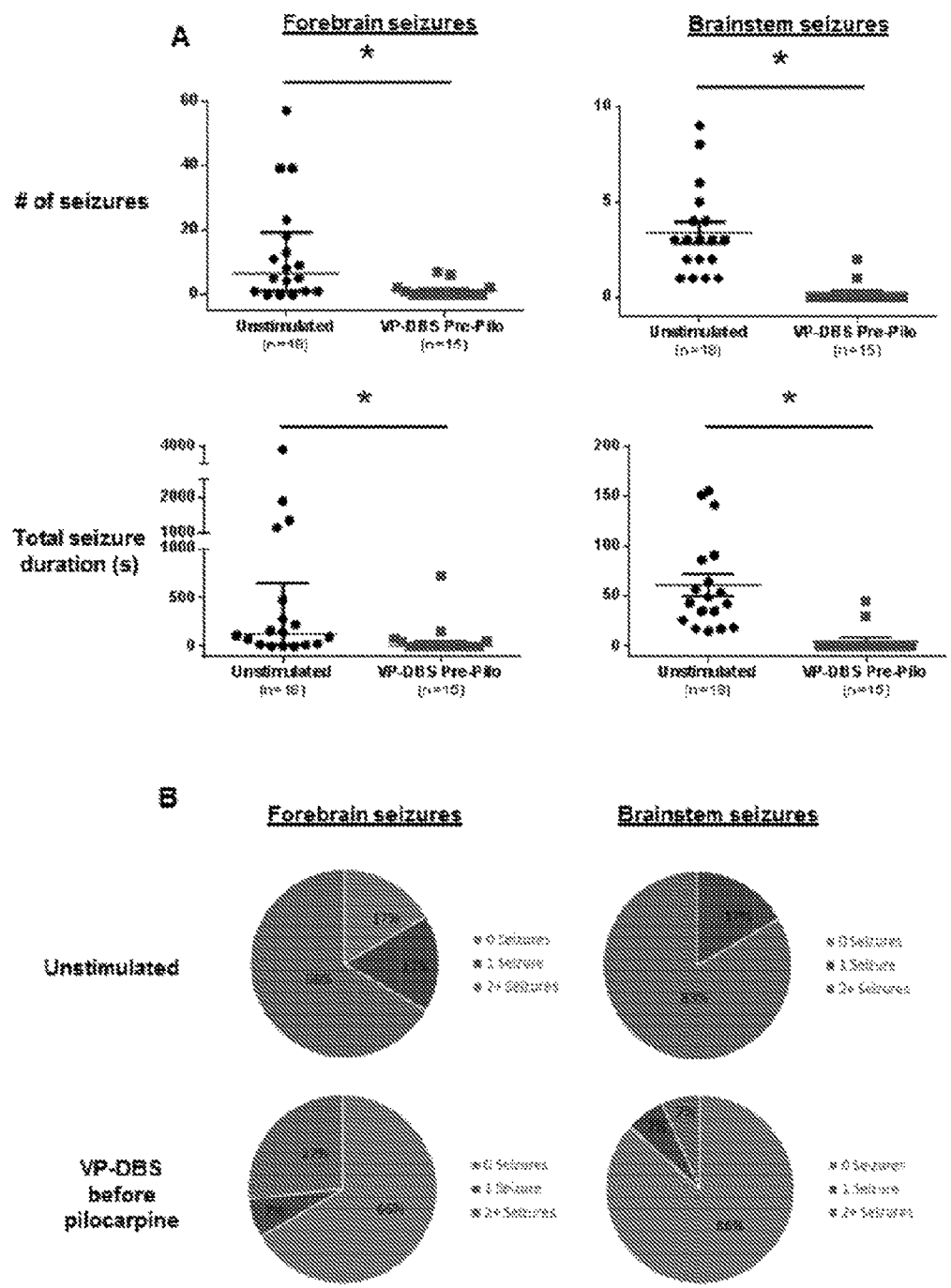

FIGS. 2A and 2B are a series of graphs showing VP-DBS before pilocarpine administration attenuates behavioral forebrain and brainstem generalized seizures. FIG. 2A shows that for 4 hours, total number (top row) and total duration (bottom row) of generalized forebrain behavioral seizures (left column) and brainstem behavioral seizures (right column) were noted in un-stimulated rats (11 naïve+7 sham rats, black dots, n=18) and rats with VP-DBS turned on 1 hour prior to pilocarpine (red dots, n=15). Each point represents data from 1 rat with median±lower and upper inter-quartile range (IQR) representing the group and asterisks represent statistical significance at p<0.05. FIG. 2B shows data from FIG. 2A as % of animals with 0 (blue slice), 1 (red slice) or >2 (green slice) behavioral forebrain (left column) and brainstem (right column) seizures from un-stimulated rats (top row) and rats with VP-DBS prior to pilocarpine (bottom row).

FIGS. 3A through 3D are a series of graphs showing that VP-DBS after pilocarpine administration and emergence of generalized behavioral brainstem seizures attenuates hippocampal, but not S1 epileptiform activity. Local field potentials (LFPs) were monitored before pilocarpine injection (baseline), after pilocarpine but prior to turning on VP-DBS and immediately after VP-DBS was turned off. Despite VP-DBS, status epilepticus persisted in the S1 in FIG. 3A with no change in amplitude in FIG. 3C or frequency in FIG. 3D. In contrast, VP-DBS attenuated the amplitude in FIG. 3C and frequency in FIG. 3D of hippocampal epileptiform events. S1 recordings were monitored from 4 rats and hippocampal recordings were from 5 other rats. Asterisks represent statistical significance at p<0.05.

Figures 4A, 4B:
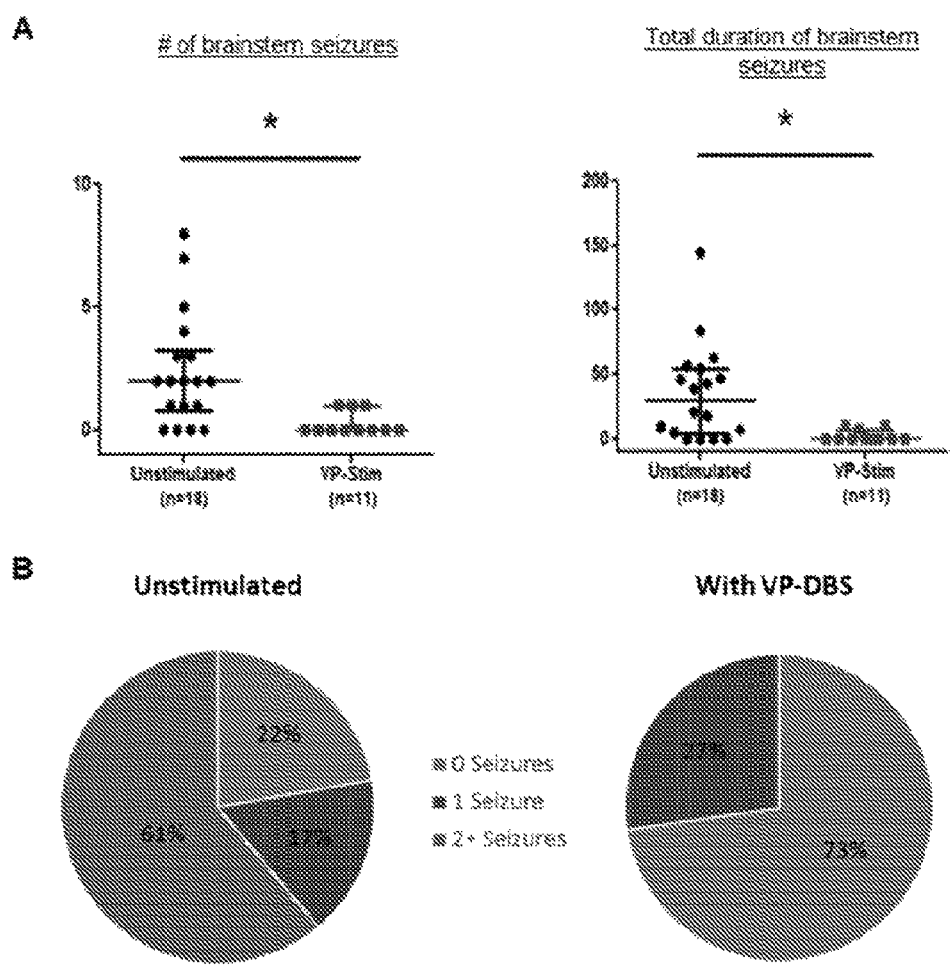

FIGS. 4A and 4B are a series of graphs showing that VP-DBS after the first generalized behavioral brainstem seizure attenuates subsequent brainstem seizures. FIG. 4A shows behavior was monitored for 4 hours after pilocarpine injection. VP-DBS was turned on after we noted the $1^{st}$ generalized behavioral brainstem, which generally occurred within 2.0-2.5 hours post-pilocarpine injection. Total number (left side) and total duration (right side) of brainstem seizures were recorded in un-stimulated rats (black dots, n=18) and rats with VP-DBS (red dots, n=11). No forebrain seizures were seen once brainstem seizures began. Each point represents data from one rat with median±IQR representing the group and asterisks represent statistical significance at p<0.05. FIG. 4B shows data from FIG. 4A represented as % of animals with 0 (blue slice), 1 (red slice) or >2 (green slice) behavioral brainstem seizures from un-stimulated rats (left pie-chart) and rats with VP-DBS after brainstem seizures began (right pie-chart).

Figures 5A, 5B, 5C, 5D, 5E:
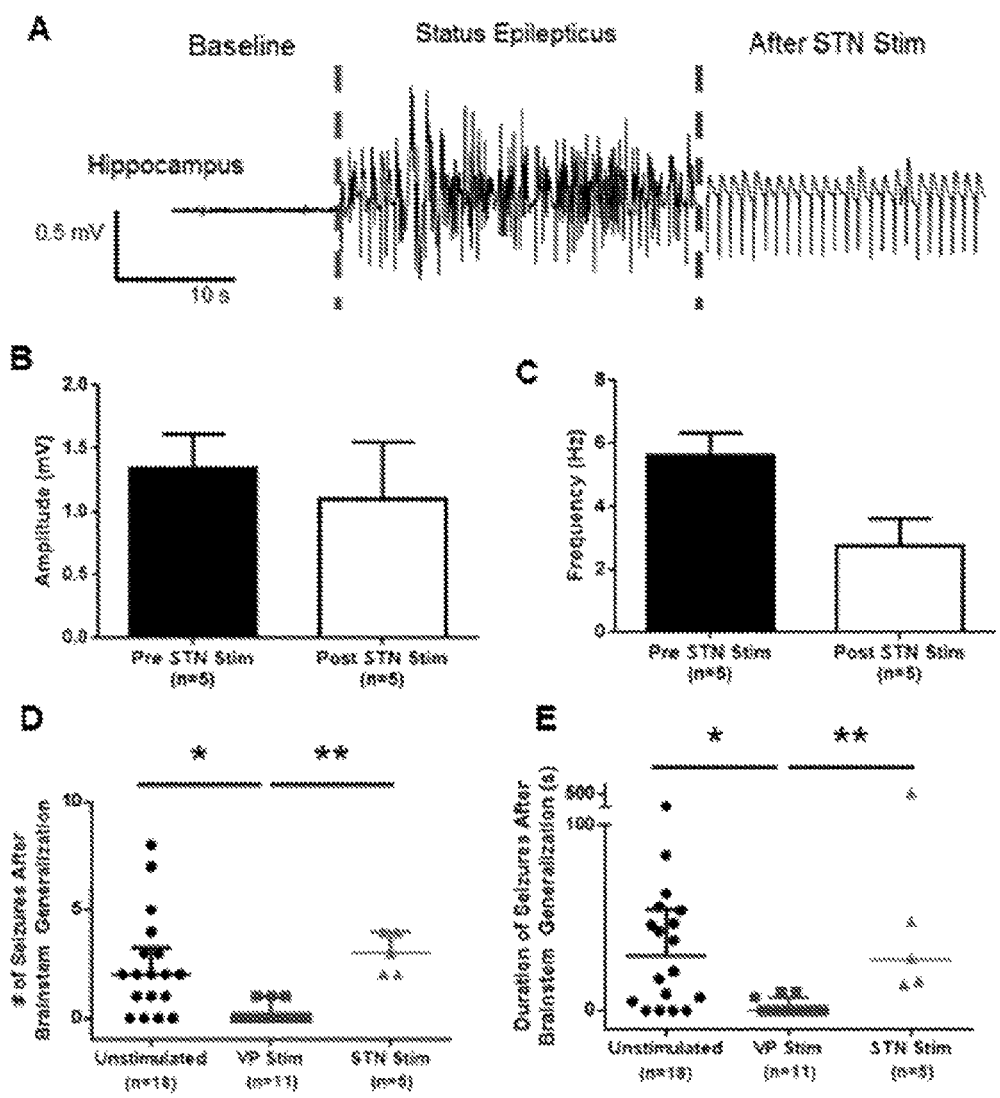

FIGS. 5A through 5E are a series of graphs showing that subthalamic nucleus (STN)-DBS does not attenuate hippocampal epileptiform activity or behavioral generalized brainstem seizures. FIG. 5A shows hippocampal LFPs were monitored before pilocarpine (baseline), after pilocarpine but prior to STN-DBS and immediately after STN-DBS was turned off. STN-DBS did not significantly change the amplitude in FIG. 5B or frequency in FIG. 5C of epileptiform events. After the $1^{st}$ generalized behavioral brainstem seizure was observed, STN-DBS was turned on and recording was continued for 1 hour. Rats with STN-DBS (green dots, n=5) did not have any significant difference in total number in FIG. 5D or duration in FIG. 5E of brainstem seizures compared to un-stimulated controls (black dots, n=18). In contrast, there were significantly fewer brainstem seizures in FIG. 5D with smaller total durations in FIG. 5E with VP-DBS (red dots, n=11). Each point represents data from one rat with median±IQR representing the group. Notably, the plots for un-stimulated rats and those with VP-DBS are the same as those shown in FIG. 4, but presented again here for easier comparison. Asterisks represent statistical significance at p<0.05.

Figure 6:
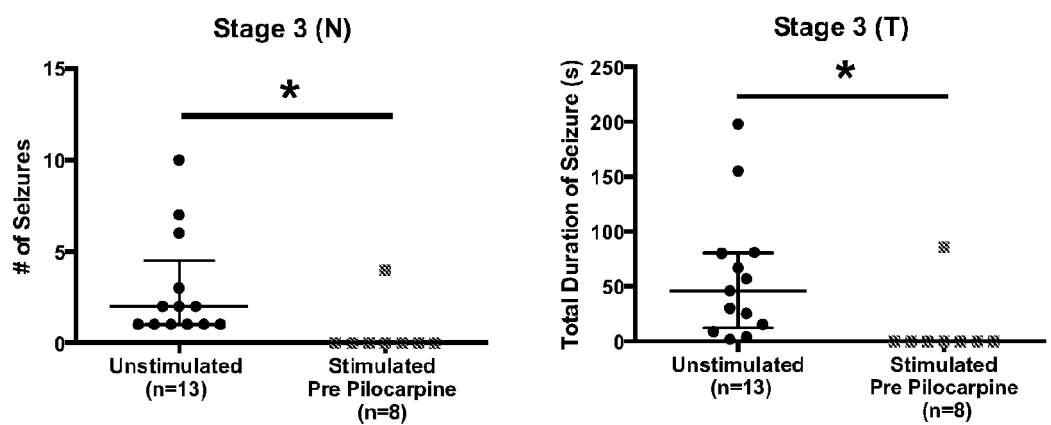

FIG. 6 is a series of graphs showing that VP-DBS applied 1 hour prior to pilocarpine and constantly throughout the monitoring period. Unstimulated animals (black dots, n=13) exhibit partial forebrain stage 3 seizures (unilateral forelimb clonus) denoted as numbers (N) and total duration (T). In contrast, VP-DBS prevented partial forebrain stage 3 seizures in 7 out of 8 animals.

Figures 7A, 7B:
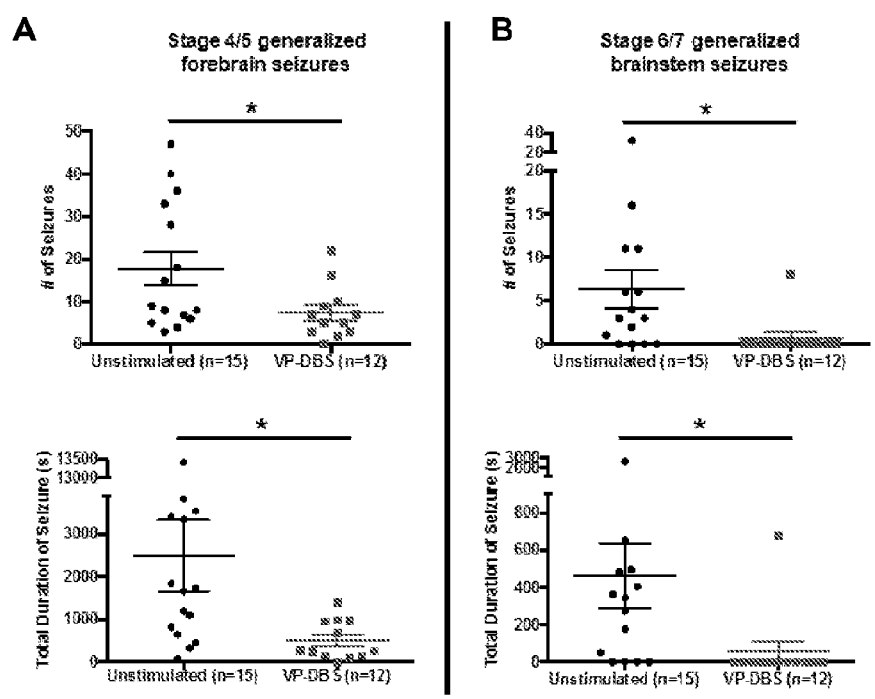

FIGS. 7A and 7B are a series of graphs showing that VP-DBS turned on immediately after the first generalized forebrain stage 4/5 seizure manifested with animals having bilateral forelimb clonus with or without falling, was able to still reduce subsequent numbers and durations of generalized forebrain seizures (stage 4/5), FIG. 7A, and could even prevent the transition to brainstem generalized seizures in 11 out of 12 animals, FIG. 7B.

Figure 8:
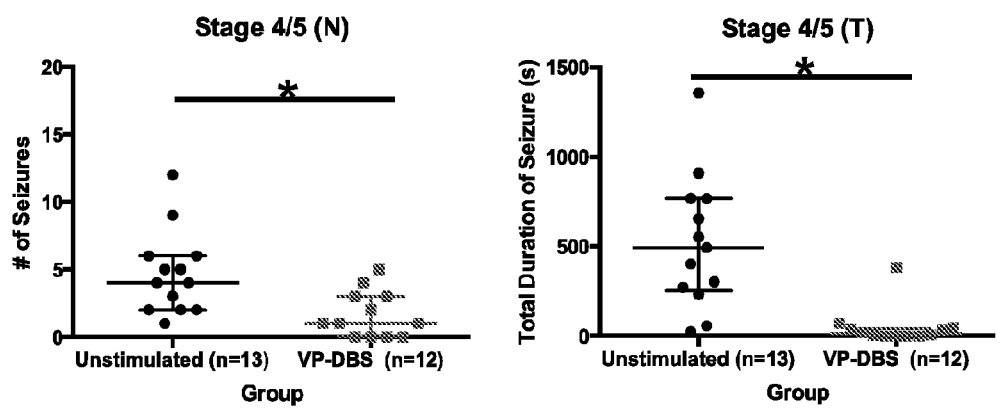

FIG. 8 is a series of graphs showing that VP-DBS turned on immediately after the first partial forebrain stage 3 seizure manifested with animals having unilateral forelimb clonus, attenuated the transition of these partial seizures into generalized forebrain seizures (stage 4/5). Black dots denote unstimulated rats with stage 4/5 generalized forebrain seizures (n=13) whereas red dots denote rats with VP-DBS having significantly less stage 4/5 seizures (N) with shorter durations (T) (n=12).

Figure 9:
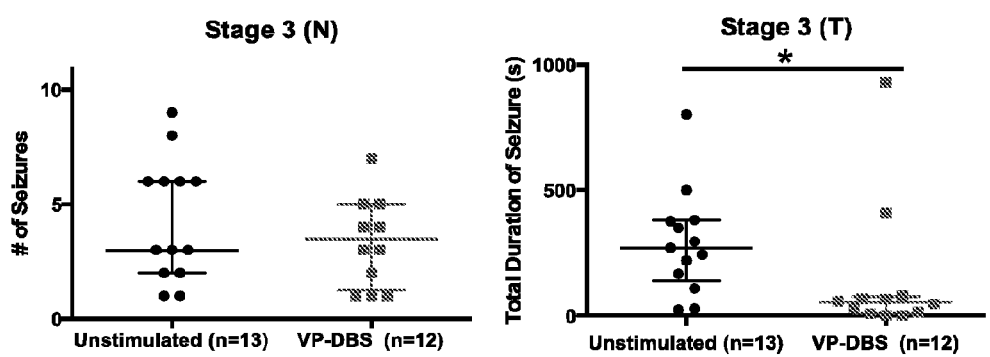

FIG. 9 is a series of graphs showing that VP-DBS turned on immediately after the first partial forebrain stage 3 seizure manifested with animals having unilateral forelimb clonus, was still able to reduce the duration of partial stage 3 forebrain seizures (T), but not their frequency (N). Black dots denote unstimulated rats with partial forebrain stage 3 seizures (n=13) whereas red dots denote rats with VP-DBS (n=12).

Figure 10:
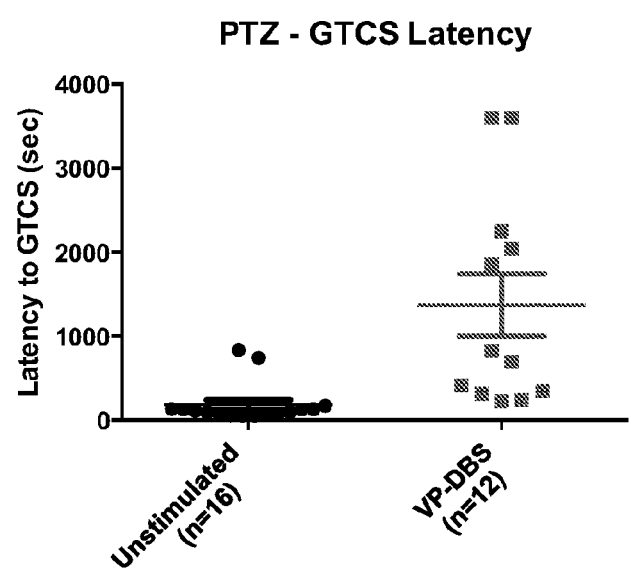

FIG. 10 is a graph showing that VP-DBS applied 30 minutes prior to pentylenetetrazol (PTZ) injection at 90 mg/kg, and constantly throughout the monitored period, increased the latency to the appearance of generalized tonic-clonic seizures (GTCSs). Unstimulated rats are denoted by black dots (n=16) while rats with VP-DBS are shown as red dots (n=12).

Figures 11A, 11B:
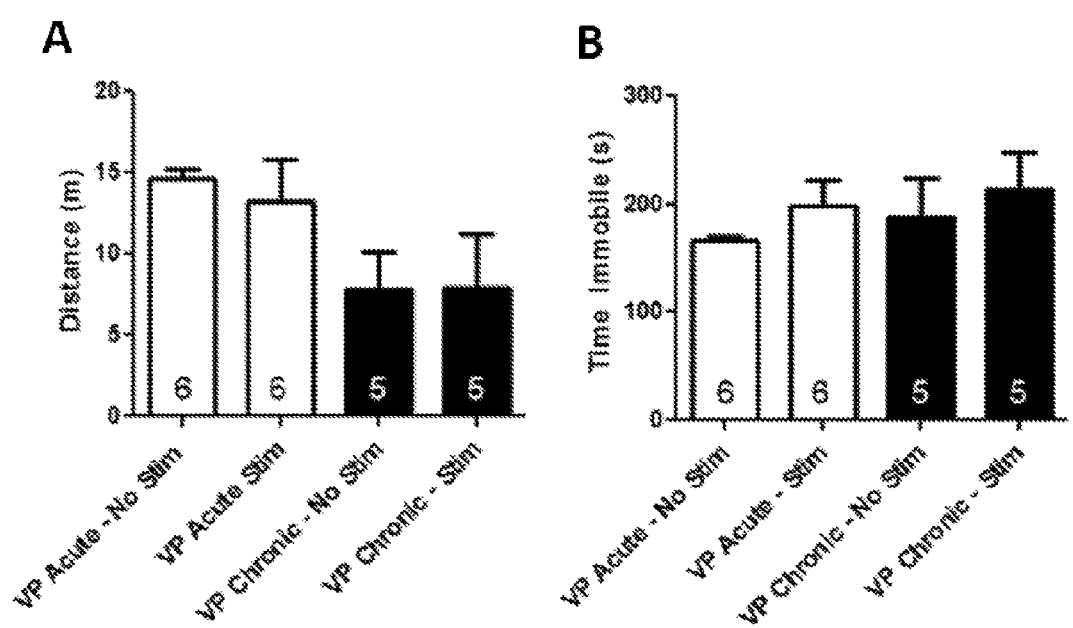

FIGS. 11A and 11B are a series of graphs showing that VP-DBS does not affect gross motor function and arousal. Rats were either stimulated for 5 minutes (acute, white bars) or 3 hours (chronic, black bars) before and during the 5 minute testing in the OFT. Numbers represent sample size of rats in each group. No significant differences were noted in either total distance traveled in FIG. 11A or time spent immobile in FIG. 11B, regardless of whether VP-DBS was off or on for 5 minutes or for 3 hours.

Figures 12A, 12B, 12C:
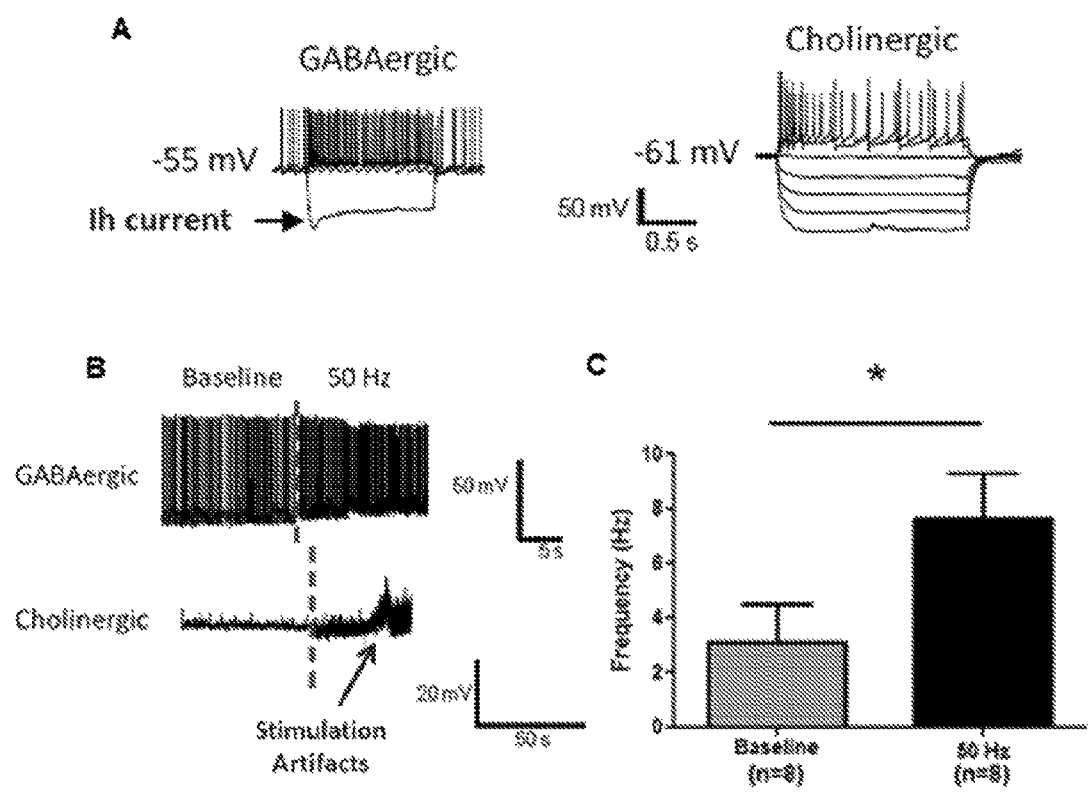

FIGS. 12A through 12C are a series of graphs showing VP stimulation at 50 Hz increased VP GABAergic neuronal firing in vitro. VP neurons were recorded with whole-cell patch clamp electrodes in brain slices. GABAergic and cholinergic neurons were identified morphologically under IR-DIC and by their distinct electrophysiological current-voltage responses including the appearance of a hyperpolarization-activated current or "$I_h$ sag" with negative current injection, indicated by the arrow in FIG. 12A. VP GABAergic neurons were tonically active and exhibited spontaneous action potentials (in FIG. 12B, left of red dotted line, "baseline"). Firing frequency of GABAergic neurons was significantly increased with 50 Hz VP stimulation (right of dotted line, "50 Hz"). Group data of action potential firing frequency from 8 VP GABAergic neurons from 4 rats before ("baseline") and during VP-DBS ("50 Hz") is shown in FIG. 12C.

Figures 13A, 13B, 13C:
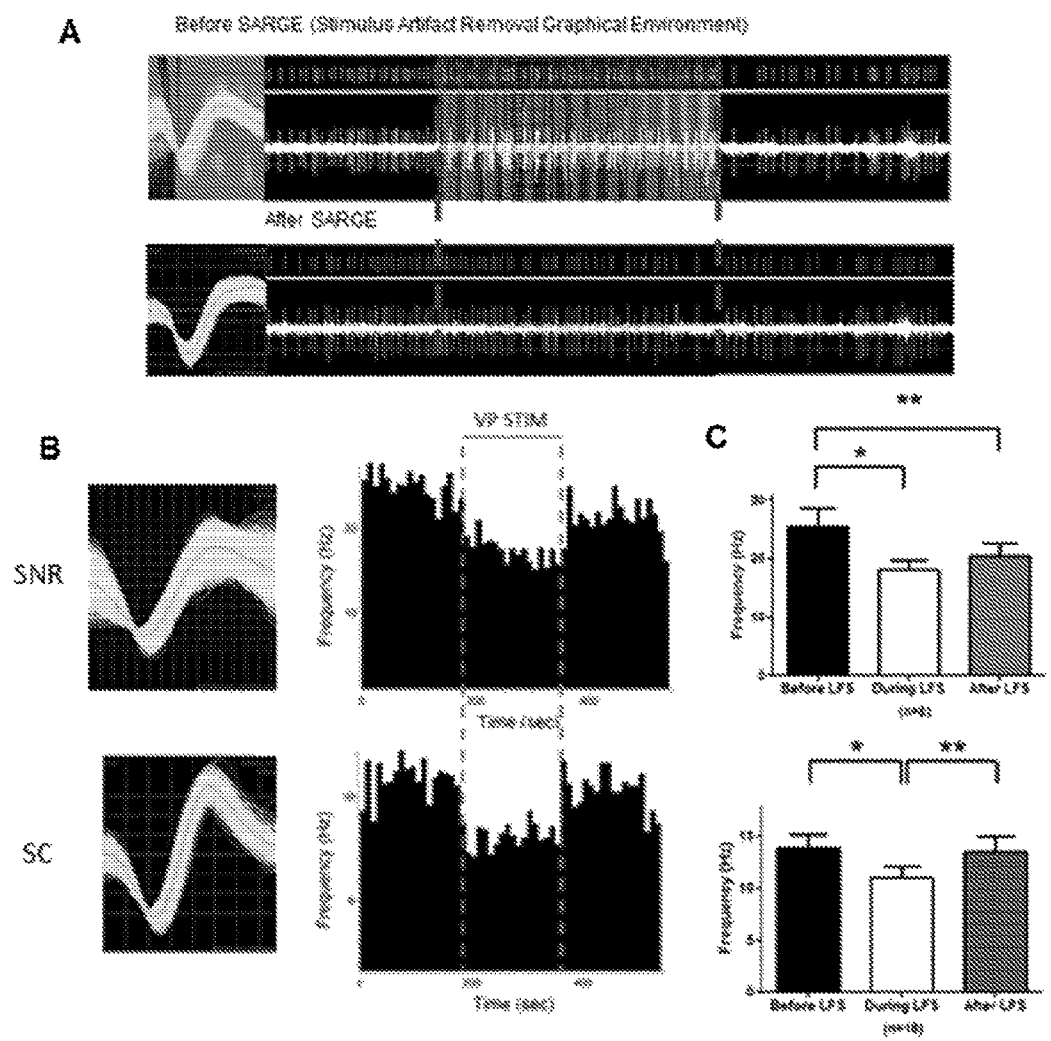
Figure 13D:
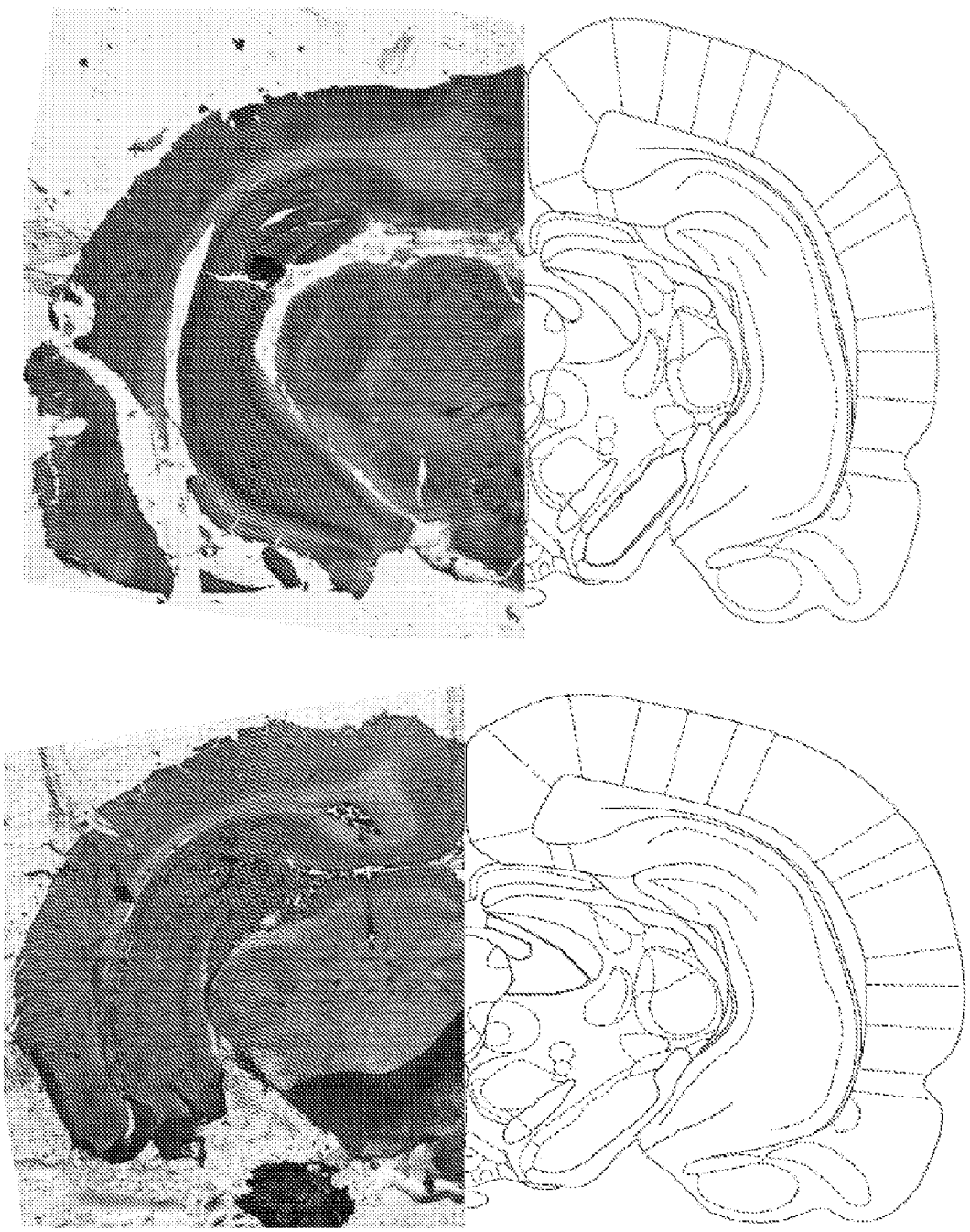

FIGS. 13A through 13C are a series of graphs showing that VP-DBS reduced SNR and SC spiking frequency in vivo. FIG. 13A shows stimulus artifacts (top trace between red dotted lines) during DBS obscured VP neuronal single-unit spiking activity, so stimulus artifact removal graphical environment (SARGE) was used to detect and remove stimulation artifacts (bottom trace). SNR and deep layer SC neurons were identified by their single-unit waveform (FIG. 13B, left side) and monitored before, during, and after VP-DBS. Single-unit spiking frequency is shown as a time-frequency histogram from a single SNR and SC neuron (FIG. 13B, right side) or as group data in FIG. 13C from 6 SNR neurons (from 3 rats) and 18 SC neurons (from 4 rats). FIG. 13D shows bilateral brain slices with the electrode placement in the SNR (left) and SC (right) is shown in red, opposite the corresponding section from a rat atlas (Paxinos, 1998) with the target brain area outlined in red.

Figures 14A, 14B:
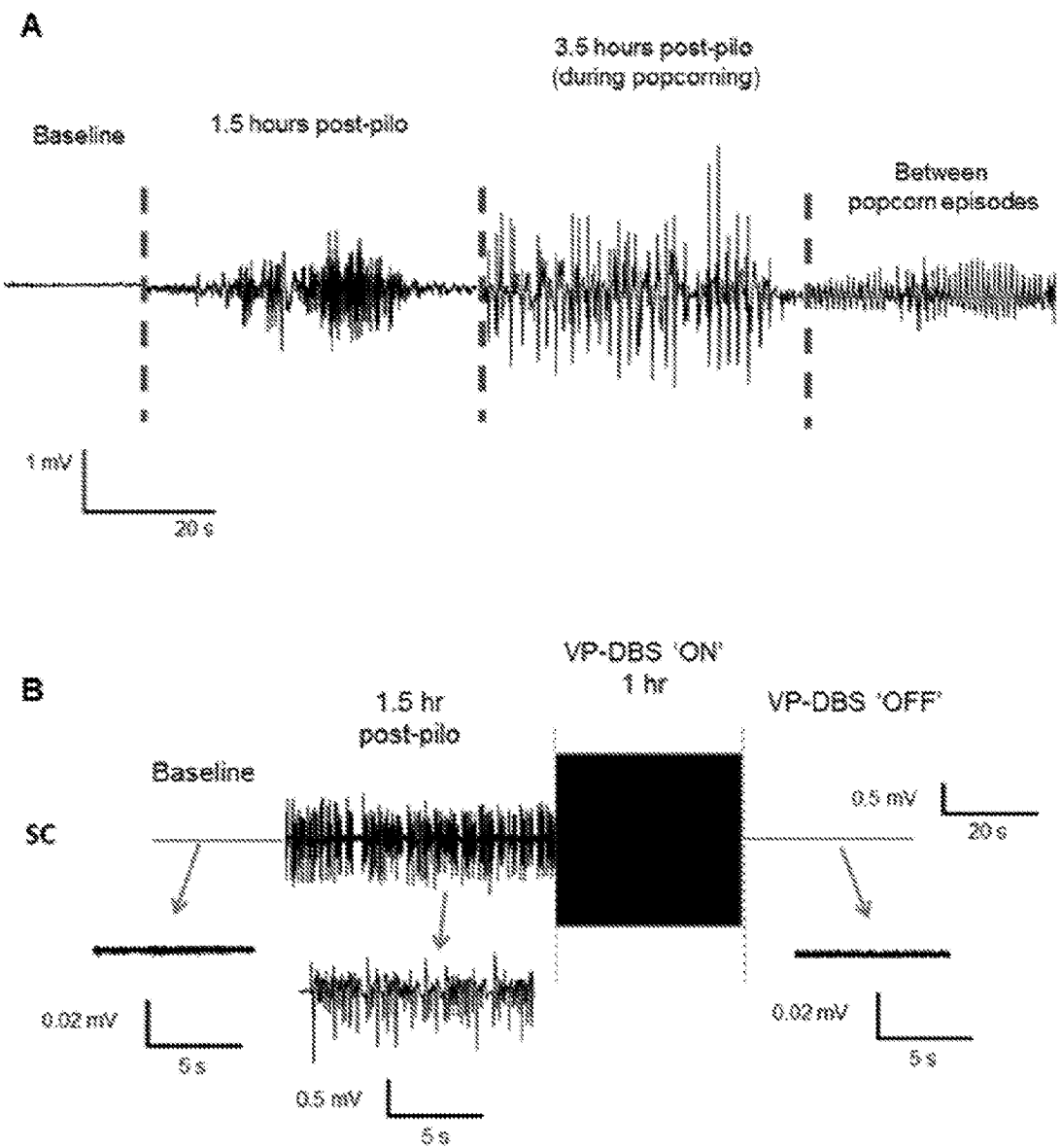

FIGS. 14A and 14B are a series of plots showing that epileptiform activity recorded in the medullary reticular formation FIG. 14A and the SC in FIG. 14B. In FIG. 14A, robust epileptiform events coincided with wild-running events while lower amplitude interictal activity was seen between episodes (n=2). In FIG. 14B, pilocarpine induced status epilepticus in the SC. VP-DBS was turned on for 1 hour, during which time the stimulus artifacts prevented any signal analysis. Immediately after VP-DBS was turned off, the SC recording resembled that of baseline, with no epileptiform activity.

Figures 15A, 15B:
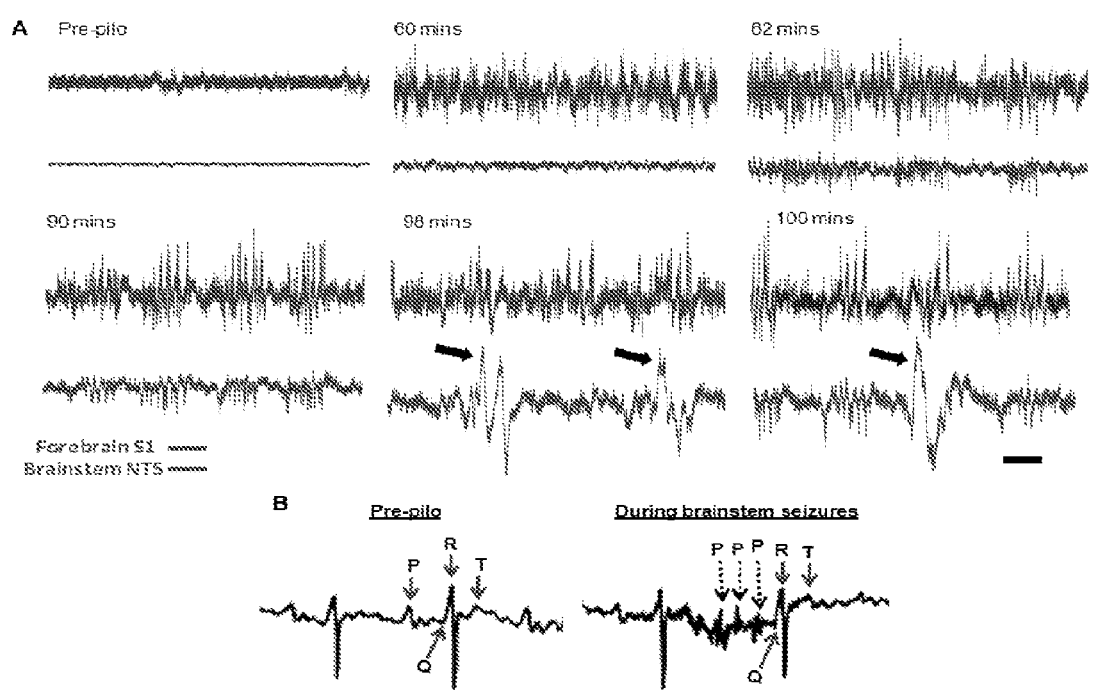

FIGS. 15A and 15B are a series of traces showing that epileptiform activity recorded in the S1 cortex and NTS in FIG. 15A and electrocardiograms (ECGs) in FIG. 15B. In FIG. 15A, there was no epileptiform activity in either the S1 cortex or NTS in rats prior to pilocarpine ('pre-pilo'). However, epileptiform activity appeared in the S1 cortex aprox. 50-60 minutes after pilocarpine administration, which then emerged in the NTS 30 minutes later and became synchronized with S1 cortical epileptiform activity. The black arrows denote direct current (DC) shifts seen only in the NTS which may represent transient acute spreading depression. In FIG. 15B, ECGs show normal heart rate waveforms (HRWs) before pilocarpine treatment (pre-pilo), but become abnormal with multiple P waves, denoted by dotted black arrows, suggestive of aberrant atrial depolarizations when epileptiform activity appeared in the S1 cortex. Their occurrence became more frequent when epileptiform activity invaded in the NTS.

Figures 16A, 16B:
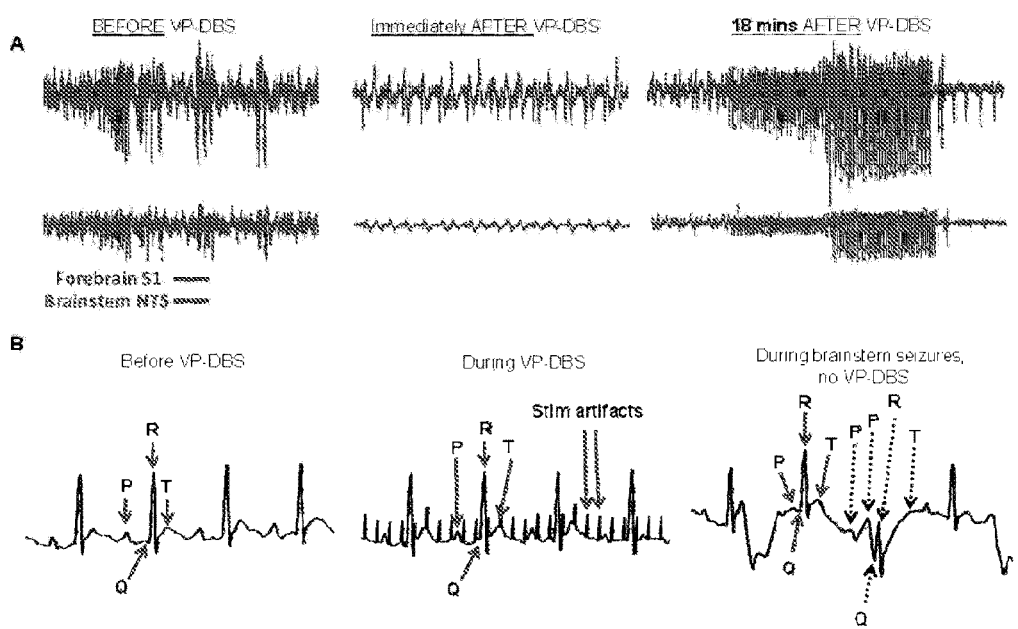

FIGS. 16A and 16B are a series of traces showing that epileptiform activity recorded in the S1 cortex and NTS in FIG. 16A and ECGs in FIG. 16B. In FIG. 16A, epileptiform activity was present after pilocarpine injection and prior to VP-DBS (left traces). However, after VP-DBS was on for 40 mins and then turned off, it was noted that S1 and NTS epileptiform activity was markedly diminished for 18 minutes and then re-emerged after. In FIG. 16B, VP-DBS was turned on when S1 and NTS epileptiform activity appeared and only few abnormal HRWs were seen during stimulation. However, 18 minutes after VP-DBS was turned off, frequent HRWs with multiple P waves were observed, which coincided with the re-appearance of S1 and NTS epileptiform activity.

DETAILED DESCRIPTION OF THE INVENTION

The present invention involves the use of deep brain stimulation of the ventral pallidum (VP-DBS) to attenuate epileptiform activity and behavioral seizures. The invention was confirmed in animal models by applying VP-DBS (50 Hz) to pilocarpine-treated rats prior to the appearance of partial or generalized forebrain seizures or after generalized brainstem seizures manifested; immediately applied after the first generalized forebrain seizure was noted or immediately applied after the first partial forebrain seizure was seen. Behavioral seizures were assessed using the Racine scale. In vitro whole-cell patch-clamp and in vivo single-unit and local field potential recording techniques were employed to unmask effects of VP-DBS on neuronal activity. Lastly, open field tests were employed to identify whether VP-DBS altered motor function or arousal state.

VP-DBS prior to pilocarpine prevented behavioral partial (n=8) and generalized forebrain seizures (n=15) and generalized brainstem seizures in most animals (n=15). VP-DBS after brainstem seizures emerged prevented or reduced the appearance of subsequent behavioral brainstem seizures (n=11). VP-DBS immediately after the first generalized forebrain seizure appeared was able to attenuate subsequent generalized forebrain seizures (n=12) and prevented the transition and appearance of generalized brainstem seizures (n=12). VP-DBS immediately after rats exhibited their first partial forebrain seizure was able to prevent the transition and emergence of seizures into generalized forebrain seizures (n=12) and was still able to reduce the duration of partial forebrain seizure (n=12). VP-DBS was also able to delay the appearance of generalized tonic-clonic seizures (GTCSs) induced by the administration of pentylenetetrazol (PTZ). VP-DBS attenuated epileptiform activity in the hippocampus (n=5), but not in the primary somatosensory cortex (S1) (n=4) in vivo once brainstem seizures emerged. Electrical stimulation in the VP increased VP GABAergic neuronal firing activity from 3.1±1.4 Hz to 7.6±1.7 Hz (n=8) in vitro and reduced substantia nigra reticulata (SNR) and superior colliculus (SC) neuronal spiking activity from 25.4±3.3 Hz to 18.2±1.4 Hz (n=6) and 18.2±1.4 Hz to 11.0±1.1 Hz (n=18), respectively, in vivo. Lastly, epileptiform activity in brainstem areas such as the reticular formation and SC was abolished with VP-DBS in awake or anesthetized and paralyzed seizing rats, respectively. VP-DBS also prevented epileptiform activity in the nucleus of the solitary tract (NTS) in anesthetized rats administered pilocarpine; the NTS is a brainstem area that controls cardiovascular function. VP-DBS prevented NTS epileptiform activity which coincided with a decrease in abnormal heart rate waveforms (HRWs). Prior to VP-DBS, many HRWs were noted when epileptiform activity propagated into the NTS. VP-DBS can be a novel therapeutic approach for individuals with intractable epilepsy and potentially prevent or diminish sudden unexpected death in epilepsy (SUDEP) by preserving activity of brainstem neurons involved in cardio-respiratory function.

Example 1

Materials and Methods

Animals and Surgery

All animal use was in compliance with the guidelines of the National Institutes of Health and Albany Medical College (AMC) Animal Care Committee. Animals were purchased from Taconic (Germantown, N.Y.) and all procedures were performed during the light phase of the light dark cycle (7:00 AM-7:00 PM, lights on).

Male Sprague Dawley rats weighing 225-350 g were anesthetized with 2% isoflurane using an inhalant system (Harvard Apparatus, Mass., USA) in a stereotaxic frame (David Kopf Instruments, Calif., USA). Body temperature was maintained at 37° C. throughout the surgery (Harvard Apparatus, Mass., USA). After, burr holes were made in the cranium according to the target brain coordinates. Stainless steel twisted wire electrodes (125 µm diameter, Plastics One, Va., USA) were implanted bilaterally in the VP (from bregma: 0.3 mm posterior, 2.5 mm lateral, and 7.0 mm ventral from dura) or the STN (from bregma: 4.16 mm posterior, 2.4 mm lateral, and 8.0 mm ventral from dura). A screw electrode was implanted in the primary somatosensory cortex (S1) (from bregma: 4.3 mm posterior, 5.0 mm lateral, and 2.0 mm ventral from dura) to obtain electrocorticograms (eCoGs) with a reference screw electrode placed in the midline, anterior of bregma. A twisted wire bipolar electrode was implanted in the hippocampus (from bregma: 4.0 mm posterior, 2.4 mm lateral, and 3.2 mm ventral from dura) to obtain hippocampal LFPs. For brainstem recordings, a twisted wire was implanted in the medullary reticular formation (from bregma: 13.7 mm posterior, 2.0 mm lateral, and 8.8 mm ventral from dura) or the superior colliculus (SC, from bregma: 5.8 mm posterior, 1.3 mm lateral, 5.0 mm ventral from dura). Dental cement (Duralay Reliance Dental, Ill., USA) was used to fasten recording electrodes, anchor screws and pedestal in place. For NTS recordings, microelectrode wires were inserted into this brainstem area at 12.5 mm posterior to bregma, 1.4 mm left of the midline and 5.4 mm below dura. Post-operatively, topical bacitracin was applied on the scalp and animals were given penicillin (80 µg/kg) subcutaneously (subQ) and buprenorphine (subQ: 0.12 g/kg) was administered every 12 hours for 72 hours post-surgery for pain management.

Stimulation and LFPs

Rats were stimulated bilaterally in the VP at 50 Hz, 300 µA, 90 µs pulse width in the cathodal configuration using a Grass S88X dual stimulator (Natus Neurology Inc, RI, USA) coupled to current isolation units (Natus Neurology Inc, RI, USA). In experiments where VP-DBS was applied prior to pilocarpine administration denoted as the "pre-pilo" group, stimulation was on for 1 hour prior to 40 mg/kg pilocarpine injection intraperitoneal (IP). LiCl (3 mEq) was IP-injected 12-18 hours prior to pilocarpine whereas 2 mg/kg scopolamine/terbutaline were IP-injected 30 minutes prior to pilocarpine. Alternatively, some animals were IP-injected only with 400 mg/kg pilocarpine to elicit seizures. After administration, VP-DBS continued for the 4 hour behavioral monitoring period. In experiments when VP-DBS was turned on after the first brainstem seizure was seen, rats in the "post brainstem-generalization" group were IP-administered pilocarpine and monitored until the first stage 6/7 brainstem seizure emerged with rats having wild-running and jumping behavior. Stimulation was then turned on and behavioral seizures were monitored for an addition 1 hour. Other experiments involved timed VP-DBS with stimulation turned on after the first stage 3 partial forebrain seizure was seen with animals exhibiting unilateral forelimb clonus or after the first stage 4/5 generalized forebrain seizures started with bilateral forelimb clonus with or without falling behavior. For STN-DBS experiments where stimulation was turned on after the first generalized brainstem seizure appeared, settings were set to 130 Hz, 300 µA, 60 µs duration in the cathodal configuration. Stimulation and recording continued for another hour before animals were sacrificed. In our last behavioral seizure and VP-DBS experiment, we investigated whether bilateral VP-DBS (at settings we use for pilocarpine) applied 30 minutes before IP-injection of 90 mg/kg PTZ and throughout the monitoring period could delay the appearance of GTCSs. For all behavioral seizure experiments, electrophysiological recordings were performed in either the S1 or hippocampus concurrently with behavioral monitoring. LFPs were obtained in the differential configuration (Model 3000, A-M Systems, Wash., USA), sampled at 1 kHz and high- and low-passed at 1 Hz and 300 Hz, respectively (MiniDigi 1B, Molecular Devices, Calif., USA).

Behavioral Testing

Behavioral seizures were scored with a Racine scale, but modified to include brainstem seizure phenotypes: 1: staring and mouth clonus; 2: head nodding; 3: unilateral forelimb clonus; 4: rearing and bilateral forelimb clonus; 5: rearing with or without falling; 6: wild-running and jumping; 7: wild-running and jumping followed by tonic-clonic seizures. In broad terms, stages 1-3 represent partial forebrain seizures; stages 4-5 are generalized forebrain seizures and stages 6-7 are generalized brainstem seizures.

To assess locomotor activity and sedation, animals were placed in a custom-made plexiglass open field apparatus (80×80×40: width×length×height in cm) for 10 min to conduct the open field test (OFT). Testing was done in the light and animal behavior was recorded with a video camera.

Total distance traveled and percent time immobile were analyzed with Any-maze software (Stoelting Co., Ill., USA).

In Vitro Whole-Cell Recordings

Sprague dawley rat pups at postnatal days 12-18 were anesthetized with 1.2 g/kg urethane and then transcardiac-perfused in dissecting solution containing (in mM): 87 NaCl, 2.5 KCl, 1.25 $NaH_2PO_4$, 7 $MgCl_2$, 0.5 $CaCl_2$, 24 $NaHCO_3$, 25 glucose and 75 sucrose (oxygenated with 95% $O_2$/5% $CO_2$). Brains were sliced 400 µm thick in an angled parasagittal orientation on a vibratome VT 1200S (Leica, Ill., USA) and incubated for 1 hour prior at room temperature in oxygenated artificial cerebrospinal fluid (aCSF) containing (in mM): 125 NaCl, 2.5 KCl, 1 $MgCl_2$, 1.25 $NaH_2PO_4$, 1 $CaCl_2$, 25 $NaHCO_3$, and 10 glucose at pH 7.4, heated to 34° C. VP neurons were visualized with an Olympus BX51WI upright microscope (Olympus Optical, N.Y., USA) equipped with a 40× water immersion lens with differential interference contract optics with infrared (DIC-IR). Whole-cell patch-clamp electrodes were pulled from borosilicate capillaries (World Precision Instruments, Fla., USA) and filled with intracellular solution containing (in mM): 110 K-gluconate, 8 NaCl, 20 KCl, 1 $MgCl_2$, 0.0001 $CaCl_2$, 10 Na-HEPES, 2 Na-ATP, 0.3 Na-GTP, pH of 7.4.

A 3-5 min stable baseline was recorded prior to applying stimulation in the VP (Grass S48 stimulator, Natus Neurology Inc, Mass., USA) delivered through a 125 µm diameter biconcentric electrode (FHC, Me., USA) at a distance of <100 µm from the recorded VP neuron. Stimulation was monophasic, 60 seconds long, 50 Hz, 90 µsec duration and 3-5 V. Recordings were obtained using an Axopatch 200B (Molecular Devices, Calif., USA), which was low-pass filtered at 5 kHz and sampled at 10 kHz. Only one VP neuron was recorded from each brain slice.

In Vivo Single-Unit Recordings

Rats were anesthetized with IP-injection of 1.2-1.4 g/kg urethane and placed in a stereotaxic frame. Tungsten microelectrodes with 70 µm shaft diameter, 1 µm tip diameter, 500 kΩ impedance resistances (FHC, Bowdoin, Me.) were lowered into the SNR (from bregma: 5.8 mm posterior, 2.0 mm lateral, and 8 mm ventral from dura) or SC (from bregma: 5.8 mm posterior, 1.3 mm lateral, 5.0 mm ventral from dura) with a micropositioner (David Kopf, Tujunga, Calif.). Recordings were acquired with a multichannel acquisition system (Omniplex, Plexon, Dallas, Tex.) sampled at 40 kHz and high and low-pass filtered online at 300 Hz and 6 kHz, respectively. VP-DBS was delivered through a stimulation electrode (biconcentric at 125 µm diameter, FHC, Me., USA) using a Grass S88X dual stimulator (Natus Neurology, Inc, RI, USA) coupled to PSIU6 or SIU-C current isolation units (Natus Neurology Inc, RI, USA).

Single-units with at least a 2:1 signal-to-noise voltage threshold were identified based on their waveform (FIG. 13B, yellow waveforms) and sorted by principal component analysis (PCA) with Offline Sorter (Plexon) and analyzed with NeuroExplorer (Nex Technologies, Westford, Mass.). Stimulus artifacts were removed offline using stimulus artifact removal graphical environment (SARGE) Matlab script (FIG. 13A).

Recording Superior Colliculus (SC) Brainstem Epileptiform Activity

To record epileptiform activity in the SC brainstem area, animals were recorded while anesthetized with 300 µg/kg fentanyl and medetomidine IP and paralyzed animals with 3 mg/kg D-tubocurarine IP. In these animals, a tracheotomy was performed by making a small 1 inch long medial incision above the trachea. After, a PE 50 tube was inserted into the trachea and the animal was ventilated with a Model 680 Small Animal Ventilator (Harvard Apparatus, Mass., USA) set to 80-100 strokes/min and 3-4 mL/stroke. Epileptiform activity was induced with 400 mg/kg pilocarpine IP, administered 30 min after 2 mg/kg scopolamine and terbutaline injection.

Recording NTS Brainstem Epileptiform Activity Along with Electrocardiograms (ECGs)

Rats were anesthetized with an IP-injection of 1.2-1.4 g/kg urethane and placed in a stereotactic frame. A craniotomy was performed and an electrocorticogram (eCoG) screw electrode was placed in the S1 cortex, 2 bundled tungsten single-unit electrodes with 500 mΩ impedance resistance was positioned in the left NTS in the brainstem and stimulating electrodes comprising of twisted stainless steel wire were placed bilaterally in the VP for DBS. In addition, a stainless steel needle was placed subQ in the left thorax to record ECGs.

A 20 minute baseline simultaneous recording of S1 cortex, NTS and ECGs was done prior to IP-injection of 400 mg/kg pilocarpine. If no epileptiform activity was seen 30-45 mins post-pilocarpine, another injection of 200 mg/kg pilocarpine was given. In most cases, this was sufficient to induce epileptiform activity in the S1 cortex, which later emerged and synchronized with NTS epileptiform activity. If needed, another 200 mg/kg pilocarpine was IP-injected 30-45 mins after the second injection. As soon as these were seen in both areas, VP-DBS at settings already mentioned above in section [0031] was turned on for 40 minutes. During this time, stimulus artifacts obscured S1 and NTS recordings. Therefore, to deduce the effect of VP-DBS on epileptiform activity, VP-DBS was turned off and LFPs in both areas and ECGs were examined to see if epileptiform activity was altered.

Post-Mortem Analysis

After experiments, rats were trans-cardiac perfused with 4% paraformaldehyde and the brain was removed and placed in paraformaldehyde for 24 hours prior to immersion in 30% sucrose. Afterwards, 50-60 µm brain sections were obtained using a freezing microtome HM 400 (Microm, Zeiss, Bern, Switzerland), mounted and dehydrated on gelatin-subbed slides (Fisher Scientific, Pa., USA). Tissue was rehydrated from 100% to 0% ethanol in double-distilled water and then stained with Cresyl violet (CV) nissl staining to confirm electrode placement. Tissue slices were coverslipped and digitized with either a NanoZoomer Digital Pathology slide scanner (Hamamatsu Photonics KK, Olympus, N.Y., USA) or a PathScan Enabler IV slide scanner (Meyer Instruments, Tex., USA).

Drugs:

Pilocarpine was purchased from Cayman Chemicals (Ann Arbor, Mich.). The other chemicals were purchased from Sigma-Aldrich (St. Louis, Mo., USA) unless stated otherwise.

Statistical Analysis:

Data were statistically analyzed with SigmaStat 10 (Systat Software, Calif., USA) and graphs were made with Graphpad Prism (GraphPad Software, Inc., Calif., USA). Two-tailed unpaired t-tests, Mann-Whitney Rank Sum t-tests or repeated measures one-way ANOVA were used, depending on the experiment, to assess significance at $p<0.05$. Parametric data were represented as mean±SEM whereas non-parametric data are shown as median with lower and upper interquartile ranges shown as median (lower IQR-upper IQR).

Results

Electrode Implantation does not Alter Seizures

Behavioral generalized forebrain (stage 4/5) and brainstem (stage 6/7) seizures were monitored in naïve rats (n=11) and sham rats implanted with bilateral stimulating electrodes in the VP, but without any stimulation (n=7) (FIG. 1). These rats had similar number (p=0.80), duration (p=0.75) and latency to forebrain seizures (p=0.57) (FIG. 1A) and similar numbers (p=0.51), duration (p=0.93) and latency to brainstem seizures (p=0.71) (FIG. 1B). Therefore, they were grouped together into one control "un-stimulated" group (n=18).

VP-DBS Before Pilocarpine Prevents Seizure Onset

VP stimulation prior to pilocarpine administration was investigated to determine if it was capable of preventing seizure manifestation. Behaviorally, the first generalized forebrain seizures in unstimulated animals appeared 50.8±7.9 minutes after pilocarpine administration, which culminated into 6.5 (1.0-19.3) seizures with a total duration of 129.5 (17.0-648.5) seconds (n=18, FIG. 2A, left column). After 184.9±11.0 min post-pilocarpine injection, behavioral brainstem seizures manifested. Over the remaining time course of the experiment, un-stimulated animals had 3.0 (1.8-4.3) behavioral brainstem seizures with a cumulative duration of 46.0 (24.0-87.3) seconds (FIG. 2A, right column). Notably, the majority (66%) of unstimulated animals had multiple (>2) behavioral forebrain seizures (FIG. 2B, top left pie-chart) and 83% had more than one behavioral brainstem seizure (FIG. 2B, top right pie-chart).

In contrast, animals with VP-DBS prior to pilocarpine administration ("pre-pilocarpine" group) had 0 (0-2) behavioral generalized forebrain seizures (p=0.0010) with significantly shorter durations of 0 (0-55) seconds (n=15, p=0.0035; FIG. 2A, left column). If generalized forebrain seizures were present (which was only in 34% of stimulated rats), they appeared 52.8±4.1 minutes after pilocarpine injection (n=5 out of 15). Similarly, VP-DBS prior to pilocarpine treatment and throughout the monitoring period revealed that stage 3 partial forebrain seizures with rats having unilateral forelimb clonus were also affected. More specifically, un-stimulated rats exhibited 2 (1.0-4.5) partial forebrain seizures that lasted a total duration of 46 seconds (12.0-80.5) (n=13). In contrast, VP-DBS prevented stage 3 partial forebrain seizures in 7 out of 8 animals (FIG. 6; p=0.001 for number of seizures and p=0.002 for seizure duration). With regards to generalized brainstem seizures, VP-DBS prevented these seizures in 13 of 15 animals (p<0.0001, FIG. 2A, right column & FIG. 2B, lower right pie-chart). Generalized brainstem seizures appeared 185.0 and 185.5 minutes after pilocarpine administration in the other two rats with VP-DBS.

Figures 3A, 3B, 3C, 3D:
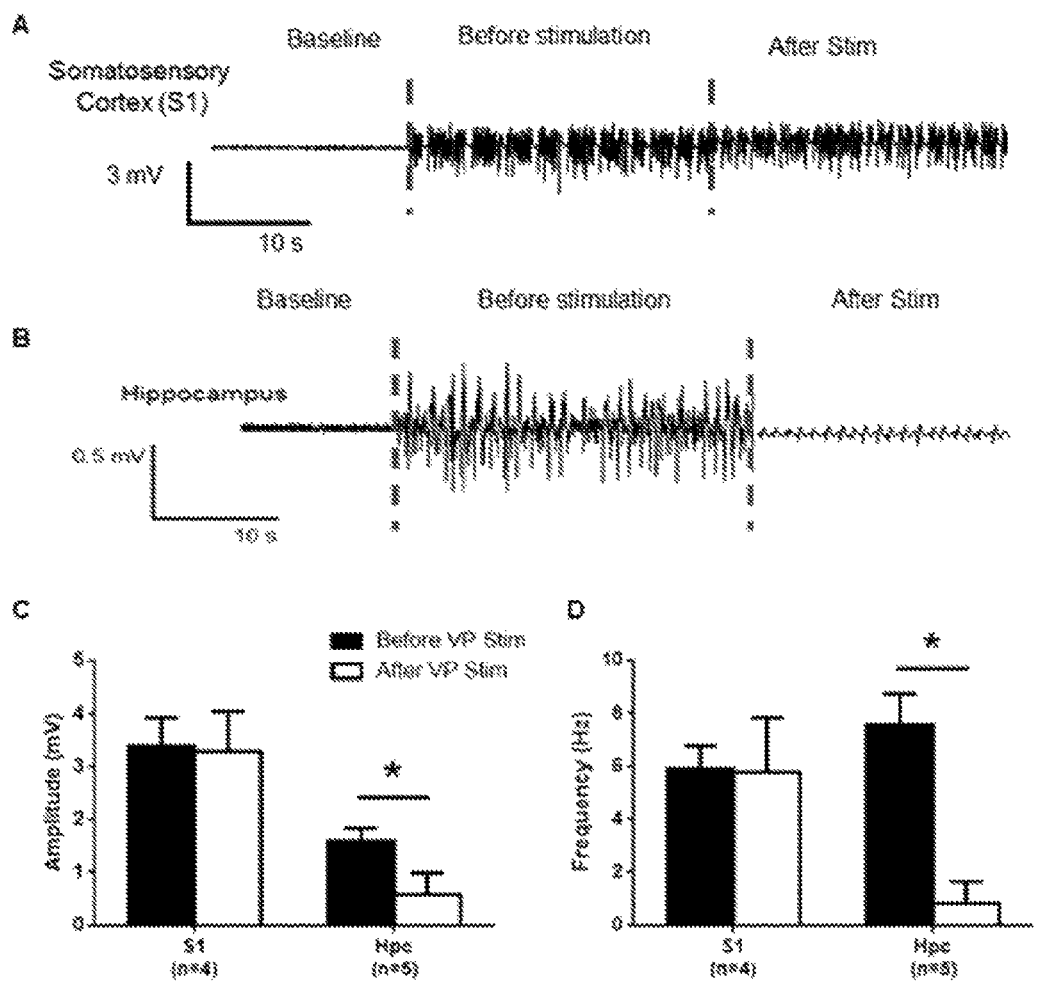

VP-DBS after Brainstem Seizures Attenuates Hippocampal Epileptiform Activity and Recurrent Behavioral Brainstem Seizures In a second group of animals, VP-DBS was examined whether it could be effective even after status epilepticus and behavioral brainstem seizures manifested. After pilocarpine administration, but prior to behavioral generalized brainstem seizures, status epilepticus emerged in the S1 (n=4) and hippocampus (n=5) cortices (FIG. 3A, "before stimulation") with epileptiform activity amplitudes of 3.4±0.5 mV (FIG. 3C) and frequencies of 5.9±0.9 Hz (FIG. 3D) in the former and epileptiform activity amplitudes of 1.6±0.3 mV (FIG. 3C) and frequencies of 7.6±1.2 Hz in the latter (FIG. 3D). After the first behavioral brainstem seizure, VP-DBS was turned on for 1 hr. Electrophysiological recordings were examined immediately after stimulation was turned off to avoid confounding stimulation artifacts. The amplitude (3.3±0.8 mV, p=0.58) and frequency (5.8±2.1 Hz, p=0.96) of epileptiform activity in the S1 was unchanged (FIGS. 3A, C, and D), but hippocampal amplitude (0.6±0.4 mV, p=0.046) and frequency (0.8±0.5 Hz, p=0.011) were diminished (FIGS. 3B, C, and D).

Behaviorally, 61% of un-stimulated animals had >2 more brainstem seizures, 17% had 1 brainstem seizure, and 22% did not exhibit any more brainstem seizures (FIG. 4B, left pie-chart). Specifically, unstimulated rats continued to have 3.0 (1.8-4.3) brainstem seizures with a cumulative duration of 46.0 (24.0-87.3) seconds (n=18, FIG. 4A). The latency to the second generalized brainstem seizure was 25.3±5.2 minutes after the first brainstem seizure (n=14). No generalized forebrain seizures were seen after brainstem seizures manifested. With VP-DBS, the number of brainstem seizures was reduced to 0 (0-1) (n=11, p=0.0019) and seizure duration was shortened to 0 (0-7) seconds (p=0.0033) (FIG. 4A). Of note, 8 of these 11 animals (73%) did not have any more brainstem seizures and only 3 of them (27%) had a single brainstem seizure (FIG. 4B, right pie-chart). None of these animals had more than 1 brainstem seizure during this time. The 3 animals that did have a second brainstem seizure had these 32.5±10.8 minutes after the first brainstem seizure.

STN-DBS does not Attenuate Hippocampal Epileptiform Activity or Behavioral Brainstem Seizures Inhibiting the STN with DBS is a proposed neuromodulatory therapy for epilepsy. Since the VP directly inhibits the STN, efficacy from VP-DBS may be due to this inhibitory action on the STN. Therefore, we tested whether STN-DBS provides similar effects on hippocampal epileptiform activity and on behavioral generalized brainstem seizures in pilocarpine-treated rats.

After behavioral brainstem seizures manifested, STN-DBS was turned on for 1 hr (n=5). Prior to stimulation, the amplitude and frequency of hippocampal epileptiform events were 1.3±0.3 mV and 5.6±0.7 Hz, respectively (FIGS. 5A-C). With STN-DBS, hippocampal epileptiform amplitudes and frequencies were not significantly different at 1.1±0.5 mV (FIG. 5B, p=0.6) and 2.8±0.9 Hz (FIG. 5C, p=0.07), respectively. Interestingly, these appeared to evolve as inter-ictal events (FIG. 5A).

Behaviorally, animals with STN-DBS still exhibited 3.0 (2-4) brainstem seizures (FIG. 5D) lasting a total of 28.0 (14.0-298.0) seconds (FIG. 5E). Therefore, rats with STN-DBS had significantly higher seizure occurrences (p=0.0008) and durations (p=0.0019) than rats with VP-DBS and were no different from un-stimulated control animals (FIGS. 5D & E).

VP-DBS Applied after Stage 4/5 Generalized Forebrain Seizures Attenuated Subsequent Forebrain Generalized Seizures and Prevented Generalized Brainstem Seizures VP-DBS was applied after the first stage 4/5 generalized forebrain seizures started with animals having bilateral forelimb clonus with or without falling over. It was noted how this timed stimulation approach would affect subsequent generalized forebrain and brainstem seizures. Unstimulated rats exhibited 17.8±3.9 generalized forebrain seizures lasting 2496±844.9 seconds (FIG. 7A, black dots) (n=15). These transitioned to 6.3±2.2 stage 6/7 generalized brainstem seizures lasting 463.9±174.1 seconds (FIG. 7B, black dots) (n=12). In contrast, rats with VP-DBS exhibited 7.4±1.8 generalized forebrain seizures (p=0.024) lasting 510.1±132.9 seconds (FIG. 7A, red dots; p=0.026) (n=12) and the transition to stage 6/7 generalized brainstem seizures was prevented in 11 out of 12 animals (p=0.035), with the 1 animal having brainstem seizures lasting 56.4 seconds (FIG. 7B, red dots, p=0.039).

VP-DBS Applied after the First Partial Forebrain Seizure Prevented the Generalization of Forebrain Seizures VP-DBS was applied as soon as the first stage 3 partial forebrain seizure started with rats having unilateral forelimb clonus. It was investigated how this timed approach would affect the progression of stage 3 partial seizures into stage 4/5 generalized forebrain seizures. Unstimulated rats had 4 (0.0-3.0) generalized lasting 492 (252.5-766.5) seconds (FIG. 8, black dots) (n=13). Notably, VP-DBS after partial seizures began was able to block the generalization of seizures with 5 out 12 rats with 0 generalized forebrain seizures and a group median of 1 (0.0-3.0) stage 4/5 generalized forebrain (p=0.038) lasting 13.5 (0.0-40.8) seconds (FIG. 8, red dots, p<0.0001) (n=12).

VP-DBS Applied after the First Partial Forebrain Seizure Reduced Subsequent Partial Seizures In the previous experiment, the focus was on whether VP-DBS turned on after stage 3 partial forebrain seizures started could affect the generalization of forebrain seizures. Here, it was investigated whether this timed approach was still effective in attenuating stage 3 partial forebrain seizures despite already having started. Unstimulated rats exhibited 3 (2-6) partial stage 3 forebrain seizures having unilateral forelimb clonus lasting 271 (138-379.5) seconds (FIG. 9, black dots) (n=13). Rats with VP-DBS after partial forebrain seizures started exhibited similar numbers of partial forebrain seizures as unstimulated rats (FIG. 9, red dots, p=0.636) (n=12), but their durations were significantly less with unilateral forelimb clonus lasting 53.5 (10.5-77.8) seconds (FIG. 9, red dots, right figure, p=0.022) (n=12).

VP-DBS Prior to PTZ Administration Increased the Latency for GTCSs to Appear 90 mg/kg PTZ was IP-injected to induce GTCS and we examined whether VP-DBS could affect these seizures. To accomplish this, protocols commonly used were followed and VP-DBS was applied 30 minutes prior to PTZ and throughout the monitored period. Unstimulated rats underwent GTCS 184.9±59.9 seconds after PTZ injection (FIG. 10, black dots) (n=16). In contrast, GTCSs appeared 1369±367.5 seconds after PTZ injection with VP-DBS (FIG. 10, red dots, p=0.0033) (n=12), which represents a 640% increase in latency; an unprecedented value in comparison to other neuromodulation approaches or antiepileptic drugs.

VP-DBS does not Affect Gross Motor Function and Arousal

The OFT was used to examine whether VP-DBS could affect general motor function and arousal since the VP is part of the basal ganglia (BG) and also has connections to limbic and brainstem structures. Unstimulated rats (n=6) traveled 14.7±0.6 m (FIG. 11A, "VP acute—no stim") and spent 166.1±3.4 sec immobile (FIG. 11B, "VP acute—no stim"). After receiving 5 minutes of acute VP-DBS before and during the OFT, rats did not exhibit any change in distance traveled (FIG. 11A, "VP acute stim": 13.2±2.6 m, p=0.55) or time spent immobile (FIG. 11B, "VP acute stim": 198.3±24.4 seconds, p=0.25). In a separate group of animals (n=5), it found was found that rats traveled 7.8±2.3 m without stimulation (FIG. 11A, "VP chronic—no stim") and were immobile for 187.5±35.9 seconds (FIG. 11B, "VP chronic—no stim"). After 3 hours of chronic VP-DBS, no significant differences were seen in the distance traveled (FIG. 11A, "VP chronic stim": 7.9±3.4 m, p=0.96) or time spent immobile (FIG. 11B, "VP chronic stim": 213.5±33.7 seconds, p=0.56).

VP Stimulation Increases GABAergic Neuronal Firing In Vitro

To investigate the underlying mechanism behind VP-DBS, the effect of VP-DBS on local VP neuronal activity was assessed, which is comprised of 77% GABAergic and 23% cholinergic neurons. Cholinergic neurons have larger, oval shaped somata, a more hyperpolarized resting membrane potential and are generally quiescent (FIG. 12A, right trace). In contrast, GABAergic neurons have smaller, triangular somata and are tonically active at rest due to a depolarized resting membrane potential (FIG. 12A, left trace). These neurons also have a hyperpolarization-activated cationic-gated ion channel ($I_h$) 'sag' (FIG. 12A, arrow).

At baseline, GABAergic VP neurons had a firing frequency of 3.1±1.4 Hz. With 50 Hz stimulation, this activity significantly increased to 7.6±1.7 Hz (n=8, p=0.008, FIGS. 12B & C). Interestingly, 50 Hz stimulation did not increase cholinergic neuronal firing activity (n=5, FIG. 12B).

VP-DBS Decreased Neuronal Spiking Activity in the SNR and SC

How VP-DBS affected neuronal activity in the SNR and SC was examined since these areas are hyperactive during wild running brainstem seizures. Prior to VP-DBS, SNR exhibited a baseline spiking frequency of 25.4±3.3 Hz (FIGS. 13B & C, n=6 cells from 3 rats) and SNC had a spiking frequency of 13.8±1.3 Hz (FIGS. 13B & C, n=18 cells from 4 rats). During VP-DBS, spiking activity in the SNR and SC decreased to 18.2±1.4 Hz (p=0.0118) and 11.0±1.1 Hz (p<0.0001), respectively. After VP-DBS was turned off, SNR neuronal spiking activity was still attenuated at 20.4±2.3 Hz, but SC neuronal spiking frequency returned to pre-stimulation values (13.5±1.5 Hz).

VP-DBS Prevents Epileptiform Activity in Superior Colliculus Brain Area in the Brainstem Although VP-DBS has an inhibitory effect on the SNR and SC in anesthetized, naïve animals, it is important to record from the brainstem regions of seizing, rather than naïve animals. This was attempted by recording unilaterally in the medullary reticular formation in pilocarpine-treated freely moving animals. Within the first hour and a half after pilocarpine administration, epileptiform activity could be seen in the medullary reticular formation (n=2, FIG. 14A, "1.5 hours post-pilo" segment). This epileptiform activity preceded any observable behavioral brainstem seizures. When behavioral brainstem seizures did occur, robust activity in the medullary reticular formation was seen (FIG. 14A, "3.5 hours post-pilo (during popcorning)" segment) along with lower amplitude interictal activity between wild-running/popcorn behavior (FIG. 14A, "between popcorn episodes" segment). To preclude the potential confound of movement artifact associated with the active nature of these episodes, recording was performed in the brainstem in anesthetized, paralyzed and artificially ventilated animals that had been administered pilocarpine. In these animals, recording was performed from the SC. One and a half hours after pilocarpine administration, status epilepticus was observed in the SC (FIG. 14B, "1.5 hr post pilo"). After status epilepticus was observed, VP-DBS was turned on for a period of 1 hour, during which time the stimulation artifacts prevented any signal analysis (FIG. 14B, "VP-DBS 'ON' 1 hr"). Due to this limitation, the effect of VP-DBS was examined by looking immediately after stimulation was turned off (FIG. 14B, "VP-DBS 'off'"). It was found that epileptiform activity in the SC had been abolished and LFPs had the same appearance as neural activity seen prior to pilocarpine injection.

VP-DBS Prevents Epileptiform Activity in the Nucleus of the Solitary Tract (NTS) in the Brainstem The finding that VP-DBS prevented epileptiform activity in the SC suggests that VP-DBS could mitigate brainstem dysfunction. However, a more direct approach in supporting this postulate is to determine whether VP-DBS can prevent epileptiform activity in the NTS since this brainstem area controls cardiovascular function and examine whether this diminishes or averts any dysfunction in heart activity. In pilocarpine-anesthetized rats, this experiment was performed and it was first noted that inserting a recording electrode in the NTS did not grossly affect heart rate over time prior to pilocarpine (420 beats-per-min with scopolamine over 20 mins) or cause cardiovascular-related mortality during the >2 hrs of seizure monitoring (FIGS. 15 and 16). After pilocarpine injection, epileptiform activity first emerged in the S1 cortex, later appeared in the NTS and then eventually synchronized with each other (n=4; FIG. 15A). Interestingly, recurrent high amplitude direct current shifts representing transient spreading depression (SD) appeared in the NTS, but not S1 cortex (FIG. 15A, black arrows). These exciting data mirror a similar phenomenon reported in seizing un-anesthetized mice that underwent cardio-respiratory arrest during long duration brainstem SD.

With ECGs, normal heart rate waveforms (HRWs) were seen prior to pilocarpine (FIG. 15B). Yet, after pilocarpine, there were 0.5±0.5 abnormal HRWs (min-max: 0-1.8 per min) with multiple P waves indicative of aberrant atrial depolarizations when epileptiform activity appeared in the S1 cortex (n=4; FIG. 15B). These became much more frequent when epileptiform activity appeared in the NTS (n=4; 117.4±68.7 abnormal HRWs per min; min-max: 5.45-298).

To see if VP-DBS prevents NTS epileptiform activity and cardiovascular dysfunction is averted or diminished, bilateral VP-DBS was applied for 40 mins once epileptiform activity appeared in S1 cortex since this precedes brainstem seizures. Notably, only 44 abnormal HRWs were observed during VP-DBS (n=1, FIG. 16B). To assess changes in epileptiform activity, it was difficult to view these in the S1 cortex or NTS during VP-DBS due to obscuring stimulus artifacts. Therefore, the effects on epileptiform was deduced immediately after VP-DBS was turned off. It was found that VP-DBS causes long-lasting attenuating of epileptiform activity in the NTS until eighteen minutes after VP-DBS was turned off. Then, epileptiform activity re-appeared in the S1 cortex and NTS, which coincided with 144 abnormal HRWs (n=1; FIGS. 16A and 16B).

Discussion

Whether VP-DBS could have potent seizure control in the pilocarpine rat model of TLE with secondarily generalized seizures was investigated. It was found that bilateral 50 Hz VP-DBS before pilocarpine prevented partial and generalized behavioral forebrain seizures and generalized brainstem seizures in most stimulated animals. VP-DBS after behavioral brainstem seizures manifested prevented subsequent brainstem seizures in the majority of animals and significantly reduced seizure severity in the few animals that did have seizures. Even if VP-DBS was turned on after partial forebrain seizures started, this timed approach could still reduce partial forebrain seizures but also prevented secondarily generalized forebrain seizures. If VP-DBS was turned on after generalized forebrain seizures started, it was remarkable to see that this timed approach could attenuate subsequent generalized forebrain seizures and prevented the progression to generalized brainstem seizures. VP-DBS was also effective in another chemoconvulsant animal model. Specifically, VP-DBS increased the latency for GTCSs to appear at an unprecedented value in comparison to other neuromodulatory approaches or antiepileptic drugs when PTZ was administered. Additionally, VP-DBS attenuated hippocampal epileptiform activity although S1 epileptiform activity persisted. In contrast, STN-DBS did not attenuate hippocampal epileptiform activity or prevent behavioral brainstem seizures. This finding suggests that VP-DBS may not mediate efficacy via STN modulation. Further, acute or chronic VP-DBS did not alter general motor activity or arousal state. As a potential underlying mechanism for VP-DBS efficacy, 50 Hz VP stimulation significantly increased VP neuronal firing activity in vitro and decreased SNR and SC single-unit spiking activity in vivo. Lastly, pilocarpine-induced epileptiform activity in brainstem areas such as the SC and medullary reticular formation and NTS was abolished by VP-DBS. Concomitantly, VP-DBS reduced the number of abnormal HRWs.

Since increasing VP neuronal activity with pharmacology could attenuate generalized behavioral seizures, 50 Hz VP stimulation was applied based on a premise that low to intermediate stimulation frequencies can increase proximal neuronal activity. Moreover, this frequency attenuated TLE with cortical stimulation in a clinical study and diminished hippocampal epileptiform activity in vitro. Consistent with the pharmacology study, VP-DBS increased GABAergic firing frequency, which could be due to depolarized resting membrane potentials from stimulation-induced elevated extracellular $K^+$. Elevated $K^+$ concentrations could also potentiate $I_h$ currents to further heighten GABAergic neuronal excitability. In contrast, 50 Hz stimulation did not induce firing in cholinergic neurons which is consistent with others reporting that lower frequency stimulation had little effect on cholinergic neurons.

VP-DBS decreased SNR and SC neuronal spiking activity. In a variety of different preclinical models of epilepsy, it was reported that SNR inhibition can prevent or attenuate convulsive seizures possibly via disinhibition of the SC. Consistent with this view, blocking GABAergic inhibition of the SC was antiepileptic in preclinical seizure models. However, other lines of evidence suggest SC excitation is involved in brainstem seizure manifestation. For example, genetically epilepsy-prone rats (GEPR-9s) exhibit audiogenic seizures (AGS) comprising of wild-running brainstem seizures followed by tonic extension and post-ictal depression and these can be attenuated with SC inhibition. Additionally, hyper-excitability in the SNR and SC was reported during wild running AGS. In this study, pilocarpine induced wild-running brainstem seizures akin to AGS and our single-unit recordings are consistent with the idea that decreased SNR and SC activity has antiepileptic efficacy. However, given that the SNR directly inhibits the SC, it is unclear how VP-DBS can simultaneously reduce SNR and SC neuronal spiking activity. VP-DBS may indirectly inhibit the SC by attenuating pedunculopontine nucleus (PPN) neuronal activity since the PPN has excitatory glutamatergic projections to the SNR and excitatory cholinergic projections to the SC.

VP-DBS prior to pilocarpine administration attenuated behavioral forebrain seizures and hippocampal epileptiform activity. Since the VP has a direct GABAergic projection to the entorhinal cortex (EC), it's plausible that VP-DBS accomplished this by attenuating EC neuronal activity and subsequently decreasing EC excitatory input to the hippocampus. In contrast, VP-DBS was unable to affect epileptiform activity in the S1, perhaps because continuous seizure spread from the temporal lobe may have induced secondary epileptogenesis and transformed naïve brain structures into independent secondary seizure foci as reported elsewhere. Alternatively, it may be because the VP does not mono-synaptically project to the S1 area of the forebrain.

VP-DBS prior to pilocarpine administration prevented seizure onset in many animals and markedly reduced seizure duration and frequency in those that still had seizures. Moreover, even after more than 2 hours of status epilepticus, VP-DBS was able to attenuate hippocampal status epilepticus and had potent efficacy for brainstem seizures. In contrast, bilateral DBS of the anterior thalamus (ANT-DBS) in pilocarpine-treated rats delayed the onset of generalized forebrain seizures, but did not attenuate these. In another report, bilateral ANT-DBS was unable to attenuate generalized forebrain seizures if it was turned on after these manifested. With VNS, it was reported that rats with intrahippocampal pilocarpine injection exhibited reduced behavioral forebrain seizure severity with significantly prolonged latency to seizure onset. However, seizures were not abolished.

In some of our behavioral seizures experiments, it was timed when VP-DBS was turned on; whether it was after partial forebrain seizures or when generalized forebrain seizures started. This is an innovative approach since many other studies only applied neurostimulation prior to a chemoconvulsant. For instance, ANT-DBS, VNS or RNS was turned on many minutes prior to pilocarpine or kainic acid administration in rats. VP-DBS was also turned on prior to pilocarpine or PTZ to be consistent with the research field and allow a comparison of VP-DBS efficacy with these neuromodulatory approaches. However, our data also shows that VP-DBS provides such potent seizure control that subsequent seizures are attenuated despite being turned on while they were taking place and could prevent these seizures to transition or evolve into more severe seizure phenotypes.

Altogether, the data strongly posits that VP-DBS has best-in-class efficacy for epilepsy. VNS was able to significantly dampen hippocampal and cortical epileptiform activity and elicited a 70% responder rate. In other words, VNS was able to reduce seizure frequency by 50% or more in 70% of rats given pilocarpine. RNS in rats administered pilocarpine reduced seizure duration from 887.±7.5 seconds (unstimulated) to 18.9±16.4 seconds (with RNS). ANT turned on prior to pilocarpine and throughout the monitored period was able to delay the appearance of stage 4/5 generalized forebrain seizures. Notably, none of these neuromodulatory approaches prevented forebrain seizures. In contrast, VP-DBS applied prior to pilocarpine treatment prevented partial and generalized forebrain seizures and generalized brainstem seizures. Even if partial or generalized forebrain seizures emerged, VP-DBS could still attenuate or prevent subsequent seizures. For PTZ, VP-DBS prior to administrating this chemoconvulsant and throughout the monitored period was able to increase latency to GTCS by 640%. In comparison, ANT-DBS applied in a similar manner only increased latency to GTCS by 61%.

Brainstem recordings were performed in the medullary reticular formation since previous research has shown the brainstem reticular formation to play a major role in the generation of generalized convulsive seizures. However, due to confounding movement artifacts, we recorded in anesthetized, paralyzed and artificially ventilated animals. We focused on the SC in these animals for a few reasons. First, the SC has been shown to be hyperactive during wild running brainstem seizures. Second, in experiments in anesthetized naïve animals, recording was performed from the SC and with the effect of VP-DBS on SC activity examined. The effect of VP-DBS on SC epileptiform activity was now to be examined. Third, epileptiform activity propagates from the SC to deeper structures including the reticular formation. As such, if VP-DBS could attenuate SC epileptiform activity, it could likewise protect downstream brainstem structures. Expanding on the efficacy of VP-DBS in attenuating brainstem seizures, VP-DBS may be able to minimize the risk of SUDEP by preventing or reducing epileptiform activity in the brainstem areas that are involved in cardio-respiratory function. Although the underlying pathophysiology of SUDEP is still unclear, there is considerable data suggesting that defects in cardiovascular and/or respiratory control are critical contributors to these occurrences. Presumably, epileptiform activity may invade into the brainstem areas involved in cardio-respiratory function and disrupt their activity. For instance, the pre-botzinger complex (PBC), the NTS and rostral ventrolateral medulla influence cardiac function. Notably, the preliminary data (FIGS. 15 & 16) strongly suggests that VP-DBS does prevent epileptiform activity in the NTS and diminishes abnormal HRWs. Therefore, there is cogent proof-of-concept that VP-DBS can prevent or reduce epileptiform activity in these regions during generalized seizures, diminish or mitigate cardiovascular dysfunction and ultimately minimize the risk of SUDEP. Given that SUDEP is the most common cause of death in patients with epilepsy, and current estimates suggest that the number of epilepsy-related deaths with non-traumatic and non-pathological causes is 24 times greater than the general non-epileptic population, it is apparent that minimizing SUDEP and seizure-related mortality has considerable clinical merit.

Application of the present invention to humans may be accomplished using standard neurosurgical techniques and off-the-shelf electrodes or stimulations that have been demonstrated as safe for use, such as those available from Medtronic of Minneapolis, Minn. Stimulation may be accomplished using various frequencies and either current or voltage approaches. For example, the present invention was established using an exemplary frequency of 50 Hz, but frequencies as low as 0.1 Hz and up to 100 Hz may be equally effective based on literature in the field of deep brain stimulation. Similarly, the current-based approach of the present invention using cathodic stimulation at 300 microamps could be varied from as low as 1 microamp to as high as 1000 microamps, i.e., 1 amp. It should be recognized by those of skill in the art that treatment approaches according to the present invention may be optimized through routine experimentation at various frequencies and current following the examples provided above. In addition, voltage based deep brain stimulation may also be used for the present invention. For example, voltages from 0.5 volts up to a maximum of 10 volts, with a preferred amount of 2 to 6 volts, can be used for deep brain stimulation. While the present invention was demonstrated using cathodic stimulation, anodic stimulation may also be effective. Lastly, constant VP-DBs stimulation or intermittent ON and OFF stimulation cycling or ON-demand stimulation paradigms could be used. The latter could be controlled by the programmer or via a closed-loop system that detects epileptiform activity (or other seizure-related biomarkers) in the VP or in limbic, cortical, subcortical or brainstem areas.

In conclusion, the present invention established that VP-DBS may be a novel best-in-class neuromodulatory approach to potently attenuate partial and generalized seizures, comprising of, but not limited to, TLE with or without secondarily generalized seizures. This treatment option could have clinical utility for individuals with intractable epilepsies. Lastly, VP-DBS may serve a novel and innovative approach to preventing or diminishing the occurrence of SUDEP by preventing brainstem epileptiform activity and safeguarding activity of neurons in this brain area critically involved in cardio-respiratory function.

In addition to deep brain stimulation, the present invention also encompasses other approaches to stimulating the ventral pallidum to attenuate epileptiform activity and behavioral seizures. For example, optogenetics may be used to attenuate electrographic or behavioral seizures. Optogenetics allows precise spatiotemporal control of defined cells and circuits by introducing light sensitive proteins, referred to as opsins, in the brain to cells to render the neurons sensitive to light. The neurons may then be exposed to light to modulate their activity. Using this approach, the present invention may be implemented by stimulating the ventral pallidum to attenuate epileptiform activity and behavioral seizures. For example, adeno-associated virus (AAV) or lentiviral (LV) particles may be injected into each VP hemisphere at 1 ul/min with a titer of $10^9$ to $10^{13}$ (0.5-5.0 µl). AAV/LV contain constructs of channelrhodopsins (ChRs) or halorhodopsin (eNpHRs), which are light-sensitive ion channels that can be selectively expressed in the VP with cell-specific promoters. For instance, AAV serotypes such as AV2/2 or AAV2/1 or LV particles may contain ArchT-ChR2-GFP constructs or CAG-ChR2-tdtomato with either ChRs or eNpHRs. Immediately after the viral injection, a guide cannula may be implanted into the VP. After, a fiber optic cable may be inserted into the guide cannula to deliver blue light (465 nm, max power at 637 $mW/mm^2$), yellow light (590 nm, max power at 127 $mW/mm^2$) or orange light (615 nm, max power at 350 $mW/mm^2$) at >100 msec light pulse width. Blue light can activate ChRs and hyper-excite infected cells whereas yellow or orange light activate eNpHRs to inhibit infected cell activity. In a proof-of-concept test, rats were infected with AAV2/2-hSyn-hChr2 (E123T/T159C)-mCherry serotype into the STN. Blue light stimulation induced spiking activity in STN neurons (n=8 cell from 3 rats) with temporal optical control and mCherry reporter fluorescence confirmed that ChR expression was in the STN. Thus, the same approach may be used to accomplish the optical control in the VP to prevent or attenuate partial and/or generalized seizures.

What is claimed is:

1. A method of treating a patient having seizures and that is at risk for sudden unexpected death in epilepsy (SUDEP), comprising the step of applying electrical stimulation to the ventral pallidum of the patient at a frequency of 50 Hertz for at least a first predetermined period of time that is sufficient to reduce epileptiform activity in the nucleus tractus solitarius (NTS) and prebotzinger complex (PBC) of the patent and avert cardiac disfunction associated with the patient that is at risk for SUDEP.

2. The method of claim 1, wherein the electrical stimulation comprises applying the 50 Hertz electrical stimulation at a current of at least 300 microamperes and with a pulse width of 90 microseconds.

* * * * *